(12) United States Patent
Zhang et al.

(10) Patent No.: US 7,585,855 B2
(45) Date of Patent: Sep. 8, 2009

(54) BENGAMIDES WITH A SUBSTITUTED CAPROLACTAM CYCLE, METHOD FOR THE PREPARATION THEREOF, COMPOSITIONS CONTAINING THEM AND USE THEREOF

(75) Inventors: Jidong Zhang, Paris (FR); Neerja Bhatnagar, Neshanic Station, NJ (US)

(73) Assignee: Aventis Pharma SA, Antony (FR)

( * ) Notice: Subject to any disclaimer, the term of this patent is extended or adjusted under 35 U.S.C. 154(b) by 0 days.

(21) Appl. No.: 12/194,119

(22) Filed: Aug. 19, 2008

(65) Prior Publication Data

US 2008/0318928 A1 Dec. 25, 2008

Related U.S. Application Data

(63) Continuation of application No. 11/753,154, filed on May 24, 2007, now abandoned, which is a continuation of application No. PCT/FR2005/002931, filed on Nov. 25, 2005.

(30) Foreign Application Priority Data

Nov. 29, 2004 (FR) ................................. 04 12646

(51) Int. Cl.
*C07D 223/12* (2006.01)
*A61K 31/55* (2006.01)
*A61P 35/00* (2006.01)

(52) U.S. Cl. .................. 514/212.03; 540/526; 540/527

(58) Field of Classification Search ............ 514/212.03; 540/526, 527
See application file for complete search history.

(56) References Cited

U.S. PATENT DOCUMENTS

| | | | |
|---|---|---|---|
| 4,692,522 A | 9/1987 | Parsons et al. | |
| 4,831,135 A | 5/1989 | Crews et al. | |
| 5,283,241 A | 2/1994 | Bochis et al. | |
| 6,239,127 B1 | 5/2001 | Kinder, Jr. et al. | |
| 7,153,846 B2 | 12/2006 | Hoffmann | |
| 2002/0128474 A1 | 9/2002 | Xu et al. | |
| 2007/0065929 A1 | 3/2007 | Hoffmann et al. | |
| 2007/0065932 A1 | 3/2007 | Haag-Richter | |
| 2007/0244087 A1 | 10/2007 | Zhang et al. | |
| 2007/0249584 A1 | 10/2007 | Zhang et al. | |
| 2009/0075971 A1 | 3/2009 | Zhang et al. | |

FOREIGN PATENT DOCUMENTS

| | | |
|---|---|---|
| EP | 0 687 673 A1 | 12/1995 |
| JP | 2004262793 | 9/2004 |
| WO | WO 98/35941 | 8/1998 |
| WO | WO 00/29382 | 5/2000 |
| WO | WO 01/85697 | 11/2001 |
| WO | WO 02/39990 | 5/2002 |
| WO | WO 2005/014574 | 2/2005 |
| WO | WO 2005/044803 | 5/2005 |
| WO | WO 2006/056696 A2 | 6/2006 |

OTHER PUBLICATIONS

Groweiss et al, Cytotoxic Metabolites from an Australian Collection of the Sponge Jaspis Species, J. Nat. Prod. 1999, 62, pp. 1691-1693.
Kinder, et al., Synthesis and Antitumor Activity of Ester-Modified Analogues of Bengamide B, J. Med. Chem.; 2001; 44; pp. 3691-3699.
U.S. Appl. No. 12/267,689, filed Nov. 10, 2008, Zhang et al.
Adamczeski et al, Novel Sponge-Derived Amino Acids. 5. Structures, Stereochemistry, and Synthesis of Several New Heterocycles, J. Am. Chem. Soc. 1989, 111, pp. 647-654.
Chang et al, Synthesis of optically active alpha-aminobenzolactam via an oxidative-cyclization reaction, Tetrahedron: Asymmetry 14 (2003) pp. 2081-2085.
Morton et al, Novel Solid-Phase Sythesis of 1,5-benzothiazepine-4-one Derivatives, Tetrahedron Letters 41 (2000) pp. 3029-3033.
Parsons et al, Cholecystokinin Antagonists. Synthesis and Biological Evaluation of a 3-Substituted Benzolactams, J. Med. Chem. 1989, 32, pp. 1681-1685.
Quinoa et al, Bengamides, Heterocyclic Anthelminthics from a Jaspidae Marine Sponge, J. Org. Chem. (1986) 51, pp. 4494-4497.
Ramana et al, A Carbohydrate-Based Approach for the Total Synthesis of 1,3-Polyol/alpha-Pyrone Antifungal Natural Products, J. Org. Chem. 2005, 70, pp. 8216-8219.
Slade et al, Angiotensin Converting Enzyme Inhibitors: 1,5-Benzothiazepine Derivatives, J. Med. Chem., 1985, 28, pp. 1517-1521.
Thale et al, Bengamides Revisited: New Structures and Antitumor Studies, J. Org. Chem. 2001, 66, pp. 1733-1741.

*Primary Examiner*—Bruck Kifle
(74) *Attorney, Agent, or Firm*—Jiang Lin

(57) ABSTRACT

The invention relates to the preparation of substituted caprolactams, a method for the preparation thereof, compositions containing them and the use thereof as a medicament, particularly as anticancer agents.

28 Claims, No Drawings

BENGAMIDES WITH A SUBSTITUTED CAPROLACTAM CYCLE, METHOD FOR THE PREPARATION THEREOF, COMPOSITIONS CONTAINING THEM AND USE THEREOF

The present invention relates especially to bengamides with a substituted caprolactam ring, to the process for preparing them, to compositions containing them and to the use thereof as medicinal product.

More particularly, and according to a first aspect, the invention relates to substituted caprolactams that are useful as anticancer agents.

Bengamides have been described in U.S. Pat. No. 6,239,127, US 2001/0 044 433 A1, WO 01/85697, WO 00/29382, U.S. Pat. No. 4,831,135, EP 687 673 and US 2002/128 474 A1. These documents essentially disclose analogs and derivatives of bengamide, a natural product isolated from a marine sponge, *Jaspis coriacea*.

These same products have been described in the literature: J. Org. Chem (1986), 51(23), 4494-7; J. Org. Chem. (2001), 66(5), 1733-41; J. Med. Chem. 2001, 44, 3692-9.

Kinder et al., in J. Med. Chem. 2001, 44, 3692-9, show the activity of these various bengamides. In this study, the authors explain that the presence of a lipophilic ester on the caprolactam is essential for their in vitro anticancer activity, and that N-substitution of the lactam with a methyl has no effect on the abovementioned activity.

Against all expectation, it has been found that it is possible to obtain products with significant anticancer activity by modifying the substituents borne by the nitrogen of the caprolactam.

These products correspond to formula (I) below:

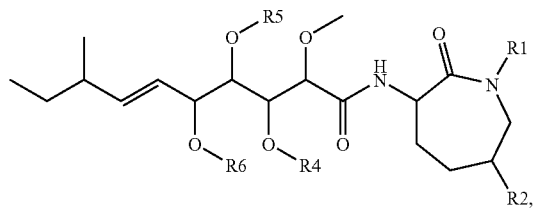

(I)

in which:
(i) R1 is independently selected from the group consisting of H, —(C1-C24)alkyl, —(C3-C9)cycloalkyl, heterocycloalkyl, —(C3-C24)alkylene, heterocycloalkylene, aryl, heteroaryl, arylalkyl, heteroarylalkyl, arylalkylene, heteroarylalkylene, —(C1-C8)alkylaryl-(C1-C24)alkyl, —(C1-C8)alkylaryl-O-(C1-C24)alkyl,
(ii) R2 is independently selected from the group consisting of H, OR7, OCO(R7), in which R7 is selected from the group consisting of —(C1-C24)alkyl, (C3-C9)cycloalkyl, heterocycloalkyl, —(C3-C24)alkylene, heterocycloalkylene, aryl, heteroaryl, arylalkyl, heteroarylalkyl, arylalkylene, heteroarylalkylene, —(C1-C8)alkylaryl-(C1-C24)alkyl, —(C1-C8)alkylaryl-O—(C1-C24)alkyl,
(iii) R4, R5 and R6 are each independently selected from the group consisting of H, —(C1-C6)acyl, —(C1-C6)alkyl, —(C1-C6)alkylaryl, —(C1-C6)alkyl-heteroaryl, -aryl, -heteroaryl, -arylalkylene, -heteroarylalkylene, with the proviso that when R4, R5 and R6 are each H, and R1 is H or methyl, then R2 is not H or OH.

Advantageously, R4, R5 and R6 are each independently selected from the group consisting of H and —(C1-C6)acyl. R4, R5 and R6 are preferably H.

A preferred R2 is chosen from H and OH, and a more preferred R2 is H.

According to one preferred embodiment, a product in accordance with the invention is of general formula (II) below:

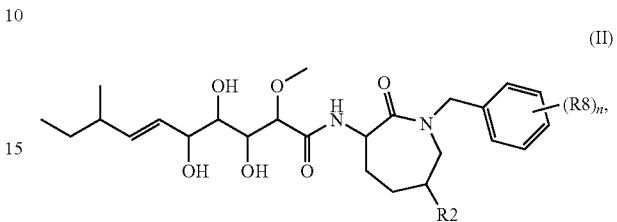

(II)

in which R8 is selected from the group consisting of H, halogen, OH, CN, O(C1-C24)alkyl, OCO(C1-C24)alkyl, —(C1-C4)alkylaryl, —(C1-C4)alkyl-heteroaryl; in which n=0, 1, 2, 3, 4 or 5, and in which R2 is selected from the group consisting of H, OH, O(C1-C24)alkyl, OCO(C1-C24)alkyl, OCO(C3-C9)cycloalkyl, —OCO(C1-C8)alkylaryl-(C0-C24)alkyl, —OCO(C1-C8)alkylaryl-O—(C1-C24)alkyl,

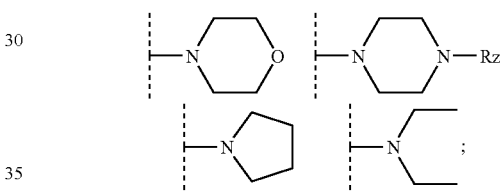

in which each Rz is independently selected from the group consisting of H, COO(R10), CONH(R10), CO(R10), R10; in which each R10 is independently selected from —(C1-C4)alkyl, —(C1-C4)alkyl halogen, —(C1-C4)alkylaryl, —(C1-C4)alkyl-heteroaryl, in which each R10 is optionally substituted with a substituent chosen from OH, halogen, —(C1-C4)alkyl, —O—(C1-C4)alkyl, —(C1-C4)alkylaryl, aryl, —(C1-C4)alkyl-heteroaryl, -heteroaryl.

A substituent R1 is advantageously chosen from —(C1-C8)alkylaryl, substituted with 0 to 5 substituents R8, which may be identical or different, chosen from H, halogen, alkyl, haloalkyl, O-haloalkyl, NH₂, aryl and heteroaryl. Even more advantageously, R1 is substituted with R8, which is selected independently from the group consisting of H, —C(CH₃)₃, F, CF₃ and OCF₃ and in which n=0, 1, 2, 3, 4 or 5. R1 is also preferably chosen from the group consisting of H, —C(CH₃)₃, F, CF₃ and OCF₃, and in which n=4 or 5.

Another preferred substituent R1 is —(C1-C8)alkylaryl in which the aryl is selected from the group consisting of:

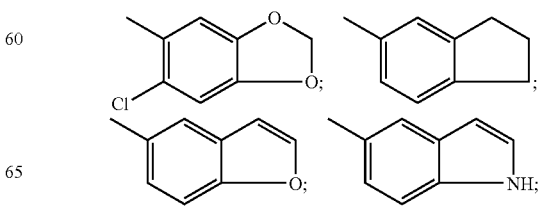

-continued

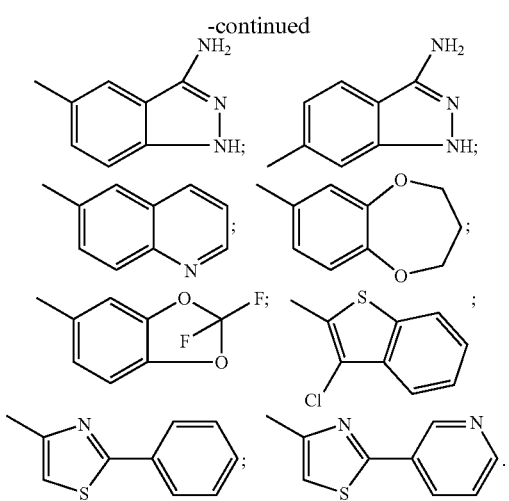

The invention preferably relates to the products illustrated in tables 1 and 2. They may exist in the form of bases, acid-addition salts, solvates, hydrates or prodrugs.

According to one particularly preferred embodiment, the absolute conformation of the carbons bearing the substituents OR3, OR4, OR5 and OR6 of a product in accordance with the invention is as presented in the general formula (III) below:

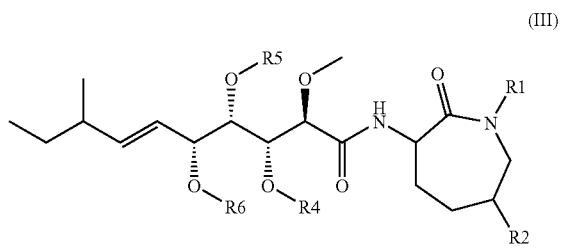

in which the substituents R1 to R6 are as defined above.

According to a second of its aspects, the invention relates to a process for preparing a product of general formula (I) below:

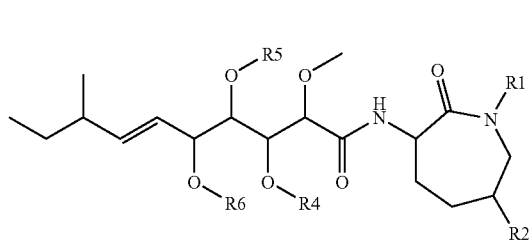

in which R1, R2, R4, R5 and R6 are as defined above, and comprising the following steps:
1) culturing and growth of *Myxococcus virescens*,
2) extraction of a bengamide-rich fraction of said culture,
3) introduction of the substituents R1 to R6 onto a product derived from the bengamide-rich fraction, to obtain a product of general formula (I).

A process according to the second aspect of the invention advantageously comprises a step of purifying the bengamide-rich fraction prior to step 3.

According to the second aspect of the invention, the bengamide-rich fraction comprises products of general formula (IV) below:

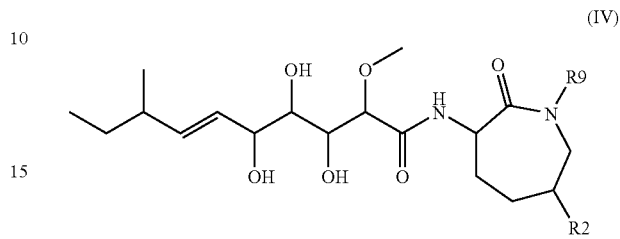

in which R9 is H or methyl, and R2 is H or OH.

Step 3 of introduction of the substituents R1 to R6 advantageously comprises a step in which the substituent R1 is introduced onto the product of general formula (IV) after protection of its free alcohol functions.

A more preferred embodiment of the invention according to its second aspect comprises a process for preparing a product of general formula (II) below:

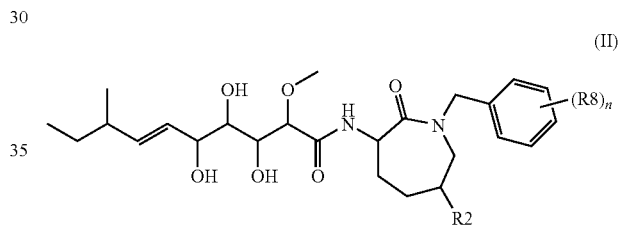

in which R2 is H or OH, and R8 is selected from the group consisting of H, halogen, OH, CN, O(C1-C24)alkyl, OCO (C1-C24)alkyl, —(C1-C4)alkylaryl, —(C1-C4)alkyl-heteroaryl; in which n=0, 1, 2, 3, 4 or 5, and in which R2 is selected from the group consisting of H, OH, O(C1-C24) alkyl, OCO(C1-C24)alkyl, OCO(C3-C9)cycloalkyl, —OCO (C1-C8)alkylaryl-(C0-C24)alkyl, —OCO(C1-C8)alkylaryl-O—(C1-C24)alkyl,

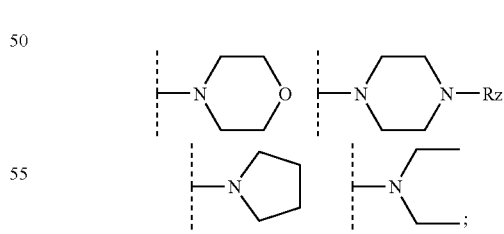

in which each Rz is independently selected from the group consisting of H, COO(R10), CONH(R10), CO(R10), R10; in which each R10 is independently selected from —(C1-C4) alkyl, —(C1-C4)alkyl halogen, —(C1-C4)alkylaryl, —(C1-C4)alkyl-heteroaryl, in which each R10 is optionally substituted with a substituent chosen from OH, halogen, —(C1-C4) alkyl, —O—(C1-C4)alkyl, —(C1-C4)alkylaryl, aryl, —(C1-C4)alkyl-heteroaryl, -heteroaryl, comprising a step in which a product of general formula (VI) below:

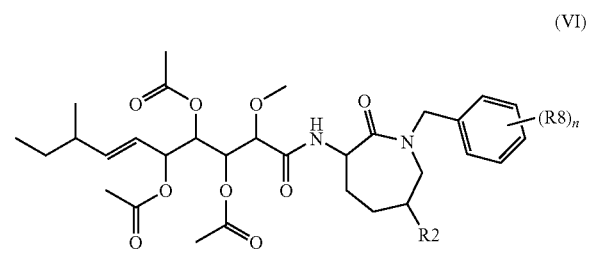
(VI)

in which R2 is H or OCOCH$_3$, and R8 and n are as defined above, is saponified to obtain a product of general formula (II).

The product of general formula (VI) is advantageously obtained by reaction between a product of general formula (V) below:

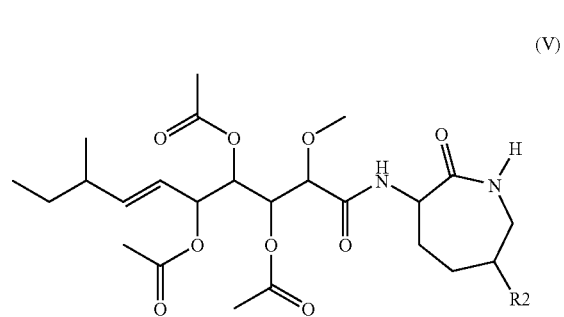
(V)

and a benzyl halide

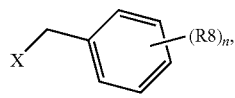

in which X is a halogen and R8 and n are as defined above, in the presence of a base.

The product of general formula (V) is advantageously obtained by acetylation of a product of general formula (IV) below:

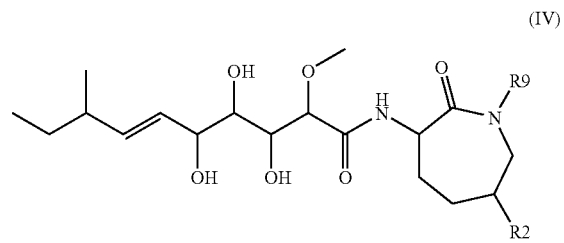
(IV)

in which R9 is H and R2 is H or OH.

According to another aspect, the invention relates to a process for preparing a product of general formula (VIII) below:

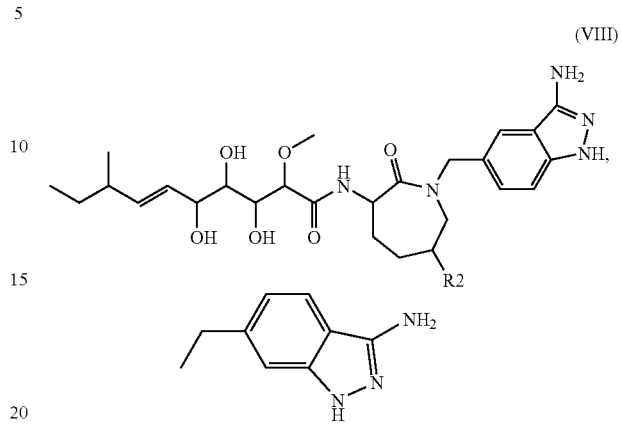
(VIII)

comprising a step in which the product of general formula (II') below:

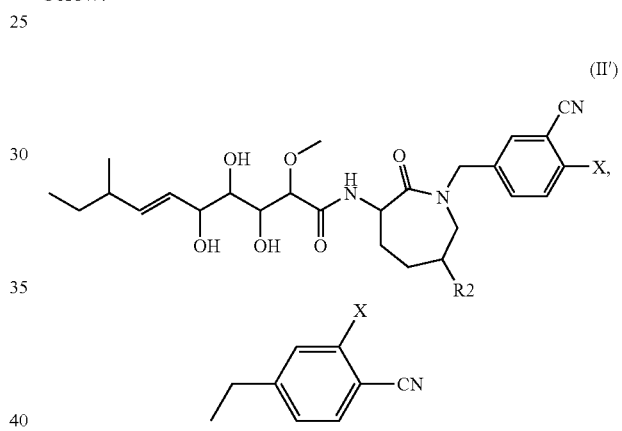
(II')

is placed in contact with NH$_2$—NH$_2$ in a solvent such as ethanol or butanol and then heated, to give the product of general formula (VIII).

According to a third aspect, the invention relates to the use of a product according to its first or according to its second aspect, for the manufacture of a medicinal product that is useful for treating a pathological condition, preferably cancer.

The products according to the invention may be in non-chiral, or racemic, form, or in a form enriched in one stereoisomer, or in a form enriched in one enantiomer; and may optionally be salified.

A product in accordance with the invention may be used for the manufacture of a medicinal product that is useful for treating a pathological condition, in particular a cancer.

The present invention also relates to therapeutic compositions containing a compound according to the invention, in combination with an excipient that is pharmaceutically acceptable according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected against the acidic medium of the stomach. The supports used for the solid forms consist especially of mineral supports, for instance phosphates or carbonates, or organic supports, for instance lactose, celluloses, starch or polymers. The liquid forms consist of solutions, suspensions or dispersions. They contain as dispersive support either water or an organic solvent (ethanol, NMP or the like) or mixtures of surfactants and solvents or of complexing agents and solvents.

The liquid forms will preferably be injectable, and, as a result, will have a formulation that is acceptable for such a use.

Acceptable routes of administration by injection include the intravenous, intraperitoneal, intramuscular and subcutaneous routes, the intravenous route being preferred.

The administered dose of the compounds of the invention will be adapted by the practitioner depending on the route of administration to the patient and said patient's condition.

The compounds of the present invention may be administered alone or as a mixture with other anticancer agents. Among the possible combinations that may be mentioned are:
  alkylating agents and especially cyclophosphamide, melphalan, ifosfamide, chlorambucil, busulfan, thiotepa, prednimustine, carmustin, lomustin, semustin, streptozotocin, decarbazin, temozolomide, procarbazin and hexamethylmelamine
  platinum derivatives especially such as cisplatin, carboplatin or oxaliplatin
  antibiotics especially such as bleomycin, mitomycin and dactinomycin
  antimicrotubule agents especially such as vinblastine, vincristine, vindesine, vinorelbine and taxoids (paclitaxel and docetaxel)
  anthracyclines especially such as doxorubicin, daunorubicin, idarubicin, epirubicin, mitoxantrone and losoxantrone
  topoisomerases of groups I and II, such as etoposide, teniposide, amsacrine, irinotecan, topotecan and tomudex
  fluoropyrimidines such as 5-fluorouracil, UFT and floxuridine cytidine analogs such as 5-azacytidine, cytarabine, gemcitabine, 6-mercaptomurine and 6-thioguanine
  adenosine analogs such as pentostatin, cytarabine or fludarabine phosphate
  methotrexate and folinic acid
  enzymes and various compounds such as L-asparaginase, hydroxyurea, trans-retinoic acid, suramine, dexrazoxane, amifostine and herceptin, and also estrogenic and androgenic hormones
  antivascular agents such as combretastatin or colchicine derivatives, and prodrugs thereof.

It is also possible to combine the compounds of the present invention with a radiation treatment. These treatments may be administered simultaneously, separately or sequentially. The treatment will be adapted by the practitioner according to the patient to be treated.

DEFINITIONS

The term "halogen" refers to an element chosen from F, Cl, Br and I.

The term "alkyl" refers to a saturated, linear or branched hydrocarbon-based substituent containing from 1 to 12 carbon atoms. The substituents methyl, ethyl, propyl, 1-methylethyl, butyl, 1-methylpropyl, 2-methylpropyl, 1,1-dimethylethyl, pentyl, 1-methyl butyl, 2-methyl butyl, 3-methyl butyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl are examples of alkyl substituents.

The term "alkylene" refers to a linear or branched hydrocarbon-based substituent containing one or more unsaturations, and containing from 2 to 12 carbon atoms. The ethylenyl, 1-methylethylenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, but-1,3-dienyl, 1-methylidenylprop-2-enyl, Z-2-methylbut-1,3-dienyl, E-2-methylbut-1,3-dienyl, 2-methyl-1-methylidenylprop-2-enyl, undec-1-enyl and undec-10-enyl are examples of alkylene substituents.

The term "alkynyl" refers to a linear or branched hydrocarbon-based substituent containing at least two unsaturations borne by a pair of vicinal carbon atoms, and containing from 2 to 12 carbon atoms. The substituents ethynyl; prop-1-ynyl; prop-2-ynyl; and but-1-ynyl are examples of alkynyl substituents.

The term "aryl" refers to a monocyclic or polycyclic aromatic substituent containing from 6 to 14 carbon atoms. The substituents phenyl, naphth-1-yl; naphth-2-yl; anthracen-9-yl; 1,2,3,4-tetrahydronaphth-5-yl; and 1,2,3,4-tetrahydronaphth-6-yl are examples of aryl substituents.

The term "heteroaryl" refers to a monocyclic or polycyclic heteroaromatic substituent containing from 1 to 13 carbon atoms and from 1 to 4 hetero atoms. The substituents pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl; and acridyl are examples of heteroaryl substituents.

The term "hetero atom" refers herein to an at least divalent atom, other than carbon. N; O; S; and Se are examples of hetero atoms.

The term "cycloalkyl" refers to a saturated or partially unsaturated cyclic hydrocarbon-based substituent containing from 3 to 12 carbon atoms. The substituents cyclopropyl; cyclobutyl; cyclopentyl; cyclopentenyl; cyclopentadienyl; cyclohexyl; cyclohexenyl; cycloheptyl; bicyclo[2.2.1]heptyl; cyclooctyl; bicyclo[2.2.2]octyl; adamantyl; and perhydronaphthyl are examples of cycloalkyl substituents.

The term "heterocyclyl" refers to a saturated or partially unsaturated cyclic hydrocarbon-based substituent containing from 1 to 13 carbon atoms and from 1 to 4 hetero atoms. Preferably, the saturated or partially unsaturated cyclic hydrocarbon-based substituent will be monocyclic and will contain 4 or 5 carbon atoms and 1 to 3 hetero atoms.

The advantages of the invention will be illustrated more particularly by the following examples:

Starting Material: Natural Bengamide (NB) (Biosynthesis)

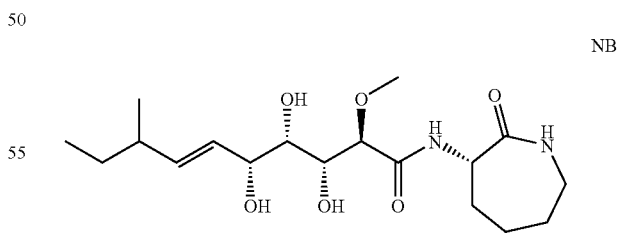

NB

The compound NB is obtained according to a method described in the as yet unpublished European patent application PCT/EP2004/011 244, the steps of which are repeated below:

Step 1: Preparation of a preliminary culture of *Myxococcus virescens* ST200611 (DSM 15898) in a conical flask.

The strain of *Mixococcus virescens* ST200611 (filed under the number DSM 15898, according to the provisions of the Treaty of Budapest, on Nov. 9, 2003, at the Deutsche Sammlung von Mikroorganismen und Zellkulturen GmbH (DSMZ), Mascheroder Weg 1b, 38124 Braunschweig, Germany). The vegetative cells of the strain DSM15898 are rod-shaped, characteristic of *Myxococcus virescens*. On solid nutrient substrates, *Myxococcus virescens* ST200611 (DSM 15898) forms orange-yellow colored fruiting organs that contain round myxospores. Instead of the strain *Myxococcus virescens* ST200611 (DSM 15898), it is possible to use mutants and/or variants that synthesize one or more of the products according to the invention.

The strain of *Mixococcus virescens* ST200611 is inoculated in 100 mL of a nutrient solution (1% fresh bakers yeast, 1% $CaCl_2.2H_2O$, HEPES 20 mM, cyanocobalamine 0.00005%, pH 7.2) in a sterile 300 mL conical flask, and the culture medium is incubated for 4 days at 30° C. on a rotary stirrer at 180 rpm. 5 mL of this culture are then used for the preparation of the main cultures.

Step 2: Preparation of a main culture of *Mixococcus virescens* ST200611 (DSM 15898).

A sterile 300 mL conical flask containing 100 mL of the following nutrient solution (0.5% yeast extract; 0.5% casitone; 0.1% $CaCl_2.2H_2O$; 0.2% $MgSO_4.7H_2O$, cyanocobalamine 0.00005%, pH 7.4) is inoculated with 5 mL of the preliminary culture prepared in step 1, or with a culture that has been grown on a fresh agar plate (1% fresh bakers yeast; 1% $CaCl_2.2H_2O$; HEPES 20 mM, cyanocobalamine 0.00005%, pH 7.2; and 1.5% agar) and is incubated at 30° C. on a stirrer at 180 rpm. The maximum production of bengamide NB is reached after 72-96 hours.

Step 3: Isolation of the compound NB, from cultures of *Mixococcus virescens* ST200611 (DSM 15898) Obtained in Step 2.

The culture medium obtained in step 2 is reproduced at a scale of 30 L of culture medium, is freeze-dried with its biomass, and the lyophilizate is extracted with twice 5 L of methanol. The methanolic extract is partially evaporated under reduced pressure to a volume of 1.2 L and is then loaded onto a 1.5 L column of CHP-20P stationary phase (MCI® gel, 75-150μ, Mitsubishi Chemical Corporation). The column is eluted with 95% methanol. The fractions are collected and their total volume is reduced to a volume of 1.5 L.

This last fraction is loaded onto a Phenomenex Luna® 10μ C18 (2) column (size: 50 mm×250 mm) comprising a Luna® 10μ C18 (2) precolumn (size: 21.2 mm×60 mm) and is then eluted (0.1% ammonium acetate, pH 4.6, adjusted with acetic acid) for 60 minutes with a gradient of from 5% to 95% of acetonitrile in water. The flow rate is 150 mL/minute and the volume of the fractions is 200 mL. Bengamides are present in fractions 5 to 14.

Step 4: Purification of the compound NB.

The fractions obtained in step 3 are freeze-dried and repurified by HPLC on a Phenomenex Luna® 10μ C18 (2) column (size: 21 mm×250 mm) having an Xterra® Prep MS C18 10 μm precolumn (Waters, size: 19×10 mm). The column is eluted with a gradient of from 5% to 40% of acetonitrile in water over 40 minutes (in the presence of 0.1% ammonium acetate, pH 8.8, adjusted with triethylamine). The aliquots (50 mL/minute) are collected in 7.5 mL fractions. Fractions 10-11 are combined and the solvents are evaporated off under reduced pressure to give 145 mg of compound NB in the form of a 70/30 mixture of diastereoisomers, purity >95%. The diastereoisomers are C16 epimers.

EXAMPLE 1

N-[(S)-1-H-2-oxoperhydroazepin-3-yl]-(E)-(2R,3R,4S,5R)-3,4,5-triacetoxy-2-methoxy-8-methyldec-6-enamide

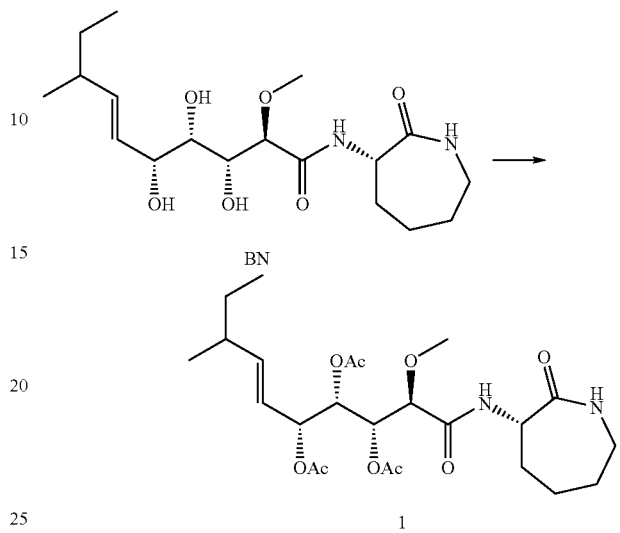

1 mL of $CH_2Cl_2$ (on siliporite) and 47.7 mg (0.128 mmol) of the compound NB are successively introduced into a 10 ml round-bottomed flask equipped with a magnetic stirrer and under an argon atmosphere. 57 μL of pyridine, 8.1 mg of DMAP and 60.4 μL of acetic anhydride are added to the solution thus obtained. The solution is stirred at room temperature and under argon. After 2 hours 30 minutes, the reaction medium is hydrolyzed with aqueous 10% $NaHSO_4$ solution and is extracted with a 4/1 (v/v) EtOAc/heptane mixture. The organic phase is dried over $MgSO_4$, filtered and then concentrated under reduced pressure. The residue obtained is purified by chromatography on silica $SiO_2$ 60 (25-40 μm, Merck), eluent: $CH_2Cl_2/MeOH$ (96/4 (v/v)). 56 mg (88%) of the expected product 1 are collected in the form of a white solid.

1H NMR spectrum (400 MHz)-δ in ppm-$CDCl_3$, mixture of isomers: 0.86 (m, 3H); 0.98 (d, J=6.5 Hz, 3H); from 1.25 to 1.60 (m, 4H); 1.90 (m, 2H); from 2.00 to 2.18 (m, 12H); from 3.25 to 3.44 (m, 2H); 3.45 (s, 3H); 3.84 (d, J=5.0 Hz, 0.2H) and 3.86 (d, J=5.0 Hz, 0.8H); 4.53 (m, 1H); from 5.28 to 5.72 (m, 5H); 5.97 (m, 1H); 7.88 (d, J=6.0 Hz, 1H).

ES+/−: 499(+)=(M+H)(+); 521(+)=(M+Na)(+); 439(+)=(M+H)−$OCOCH_3$; 997(+)=(2M+H)(+)

EXAMPLE 2

N-[(S)-1-(4-benzyl)-2-oxoperhydroazepin-3-yl]-(E)-(2R,3R,4S,5R)-3,4,5-triacetoxy-2-methoxy-8-methyldec-6-enamide

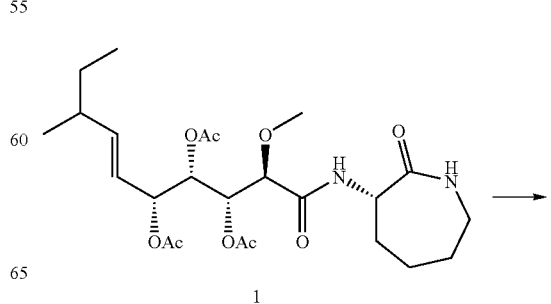

-continued

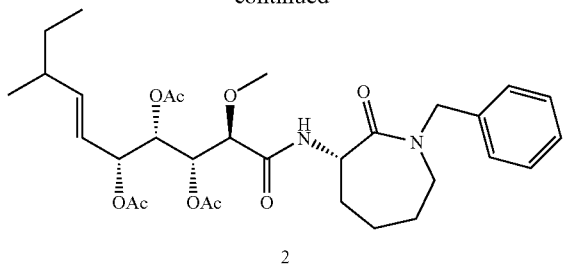

2

1 mL of DMF and 26.5 mg (53.15 μmol) of compound 1 are successively introduced into a 10 mL round-bottomed flask equipped with a magnetic stirrer and under an argon atmosphere. 3.1 mg (1.2 eq.) of 50% NaH are added to the solution thus obtained, cooled to 0° C. The reaction medium is stirred for 5 minutes and 12.64 μL (2 eq.) of benzyl bromide are then added. The reaction is continued for 4 hours and the reaction medium is then hydrolyzed with aqueous NH$_4$Cl solution and then extracted twice with an EtOAc/n-heptane mixture (1/2). The organic phase is dried over MgSO$_4$, filtered and then concentrated under reduced pressure. The residue obtained is purified by preparative chromatography (SiO$_2$ 60, Merck, eluent, CH$_2$Cl$_2$/MeOH (96/4)). 6.8 mg (21.5%) of the expected product 2 are collected.

$^1$H NMR spectrum (400 MHz)-δ in ppm-CDCl$_3$ mixture of isomers: 0.82 (m, 3H); 0.94 (d, J=6.5 Hz, 3H); from 1.10 to 2.15 (m, 18H); 3.25 (dd, J=5.5 and 14.5 Hz, 1H); 3.42 (s, 0.6H) and 3.43 (s, 2.4H); 3.51 (dd, J=11.5 and 14.5 Hz, 1H); 3.81 (d, J=5.0 Hz, 0.2H) and 3.83 (d, J=5.0 Hz, 0.8H); 4.55 (d, J=14.5 Hz, 1H); 4.63 (m, 1H); 4.74 (d, J=14.5 Hz, 1H); from 5.25 to 5.68 (m, 5H); from 7.23 to 7.37 (m, 5H); 8.05 (d, J=6.0 Hz, 1H).

ES+/−: 589(+)=(M+H)(+); 529(+)=(M+H)(+)−OAc; 1117 (+)=(2M+H)(+)

EXAMPLE 3

N-[(S)-1-(4-benzyl)-2-oxoperhydroazepin-3-yl]-(E)-(2R,3R,4S,5R)-3,4,5-trihydroxy-2-methoxy-8-methyldec-6-enamide

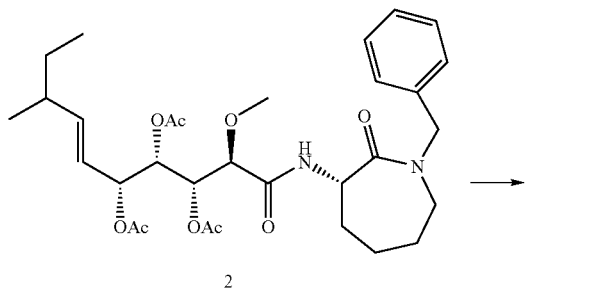

2

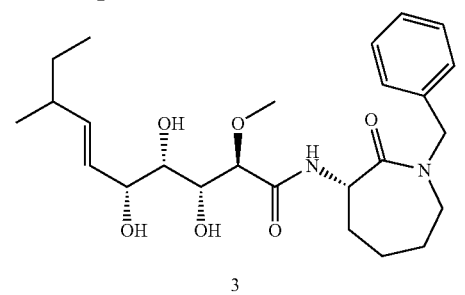

3

500 μL of methanol, 6.8 mg (11.55 μmol) of compound 2 and 4.8 mg (3 eq.) of potassium carbonate are successively introduced into a 5 ml round-bottomed flask equipped with a magnetic stirrer. The reaction medium is concentrated under reduced pressure after reaction for 1 hour 10 minutes, and the residue is then taken up in CH$_2$Cl$_2$. The insoluble material is filtered off and washed 3 times with CH$_2$Cl$_2$. The filtrate is collected, the solvents are evaporated off under reduced pressure and the residue is dried under vacuum. 5.8 mg of crude product are thus collected. This crude product is purified by TLC (SiO$_2$ 60, Merck, eluent, CH$_2$Cl$_2$/MeOH (96/4)). 3.8 mg (71%) of the expected product 3 are collected.

1H NMR spectrum (400 MHz)-δ in ppm-CDCl$_3$ mixture of isomers: 0.86 (m, 3H); 1.00 (d, J=6.5 Hz, 0.8H) and 1.02 (d, J=6.5 Hz, 2.2H); from 1.15 to 2.15 (m, 9H); from 3.00 to 3.30 (broad m, 3H); 3.48 (dd, J=11.5 and 14.5 Hz, 1H); 3.58 (s, 3H); 3.65 (broad m, 1H); 3.81 (d, J=6.5 Hz, 1H); 3.88 (broad d, J=6.5 Hz, 1H); from 4.22 to 4.80 (m, 5H); 5.49 (dd, J=6.5 and 15.5 Hz, 1H); 5.72 (m, 1H); from 7.22 to 7.39 (m, 5H); 8.20 (broad d, J=6.0 Hz, 1H).

ES+/−: 463(+)=(M+H)(+); 461 (−)=(M−H)(−)

EXAMPLE 4

N-[(S)-1-(4-tert-butylbenzyl)-2-oxoperhydroazepin-3-yl]-(E)-(2R,3R,4S,5R)-3,4,5-triacetoxy-2-methoxy-8-methyldec-6-enamide

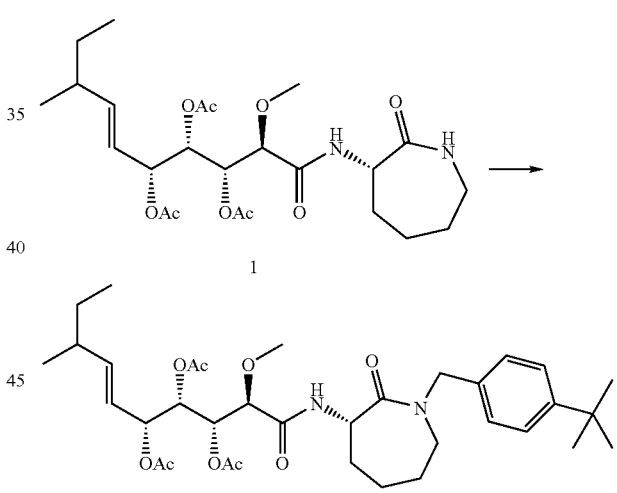

3 mL of 4-methyl-2-pentanone and 75 mg (150 μmol) of compound 1, 171 mg (752 μmol) of 4-tert-butylbenzyl bromide and 245 mg (752 μmol) of anhydrous cesium carbonate are successively introduced into a 10 ml round-bottomed flask equipped with a magnetic stirrer, and under an argon atmosphere. The reaction medium is heated for 24 hours at 50° C. The suspension is filtered and rinsed with a minimum amount of 4-methyl-2-pentanone. 68 mg (300 μmol) of 4-tert-butylbenzyl bromide and 100 mg (408 μmol) of anhydrous cesium carbonate are added to the filtrate, which is then heated for a further 20 hours at 50° C. After filtering and evaporating to dryness, 275 mg of crude product are obtained, which product is purified by preparative chromatography (SiO₂ 60, Merck-25g, 15-40 μm, eluent, EtOAc/heptane (60/40). 30 mg (31%) of the expected product 4 are obtained (Rf: 0.32).

EXAMPLE 5

N-[(S)-1-(4-tert-butylbenzyl)-2-oxoperhydroazepin-3-yl]-(E)-(2R,3R,4S,5R)-3,4,5-trihydroxy-2-methoxy-8-methyldec-6-enamide

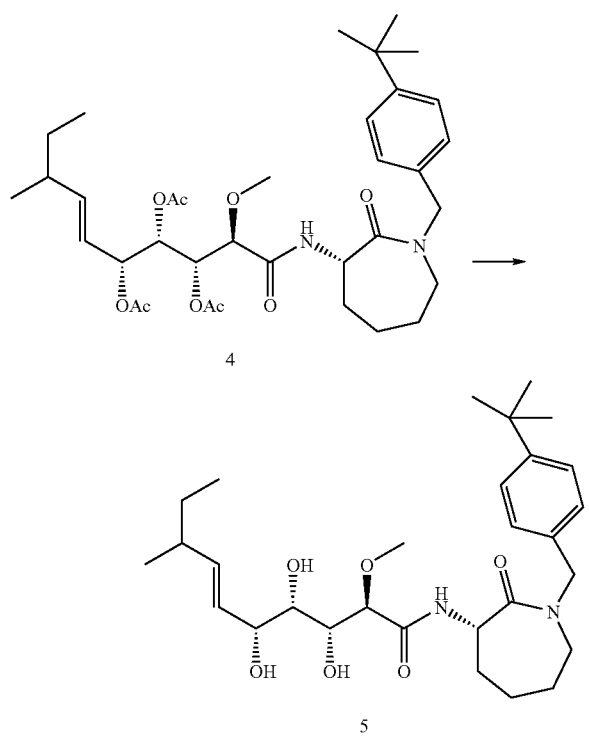

3 mL of methanol, 29 mg (45 μmol) of compound 4 and 20 mg (144 μmol, 3.2 eq.) of potassium carbonate are successively introduced into a 10 ml round-bottomed flask equipped with a magnetic stirrer. The reaction medium is stirred for 3 hours, at room temperature, and is then taken up in methylene chloride and washed with water. The organic phase is dried over sodium sulfate, filtered and evaporated to dryness under vacuum. 21 mg (90%) of the expected product 5 are obtained.

1H NMR spectrum (400 MHz)-δ in ppm-DMSO-d6, mixture of 2 isomers (70%-30%): 0.81 (t, J=7.5 Hz, 2.1H); 0.82 (t, J=7.5 Hz, 0.9H); 0.93 (d, J=7.0 Hz, 0.9H); 0.94 (d, J=7.0 Hz, 2.1H); 1.14 (m, 1H); from 1.21 to 1.31 (partially masked m, 2H); 1.26 (s, 9H); 1.39 (m, 1H); from 1.58 to 1.70 (m, 2H); 1.81 (m, 1H); 1.89 (m, 1H); 1.99 (m, 1H); from 3.20 to 3.38 (partially masked m, 2H); 3.28 (s, 3H); from 3.51 to 3.62 (m, 2H); 3.71 (d, J=7.5 Hz, 1H); 3.98 (m, 1H); from 4.35 to 4.48 (m, 3H); 4.56 (d, J=5.0 Hz, 1H); from 4.58 to 4.65 (m, 2H); 5.38 (m, 1H); 5.48 (dd, J=7.5 and 15.5 Hz, 1H); 7.19 (broad d, J=8.5 Hz, 2H); 7.34 (broad d, J=8.5 Hz, 2H); 7.92 (d, J=6.5 Hz, 1H).

ES: 519(+)=(M+H)(+)

EXAMPLE 6

N-[(S)-2-oxo-1-(3-trifluoromethylbenzyl)perhydroazepin-3-yl]-(E)-(2R,3R,4S,5R)-3,4,5-triacetoxy-2-methoxy-8-methyldec-6-enamide

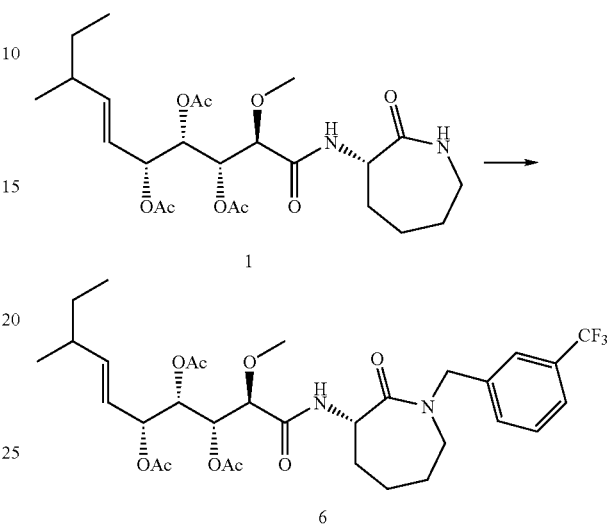

1.5 mL of 4-methyl-2-pentanone and 60 mg (120 μmol) of compound 1, 144 mg (600 μmol) of trifluoromethylbenzyl bromide and 196 mg (600 μmol) of anhydrous cesium carbonate are successively introduced into a 10 ml round-bottomed flask equipped with a magnetic stirrer, and under an argon atmosphere. The reaction medium is heated for 20 hours at 50° C. It is allowed to cool to room temperature and is then poured into a suspension of 10 ml of ethyl acetate and 5 ml of saturated aqueous ammonium chloride solution. After separation of the phases by settling, the aqueous phase is re-extracted with ethyl acetate. The organic phases are combined and dried over sodium sulfate. After filtering and evaporating to dryness, 189 mg of crude product are obtained, which product is purified by preparative chromatography (SiO₂ 60, 8 g 40-60 μm Biotage cartridge, eluent: EtOAc/heptane (50/50). 41 mg (52%) of the expected product 6 are obtained (Rf: 0.28).

EXAMPLE 7

N-[(S)-2-oxo-1-(3-trifluoromethylbenzyl)perhydroazepin-3-yl]-(E)-(2R,3R,4S,5R)-3,4,5-trihydroxy-2-methoxy-8-methyldec-6-enamide

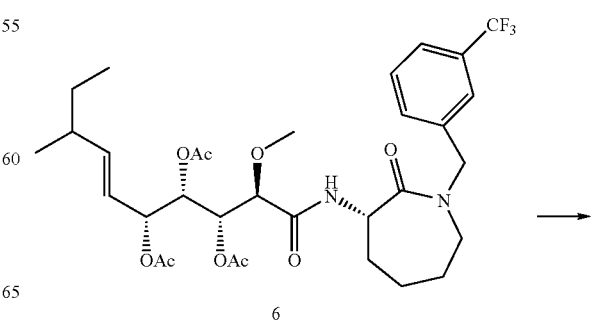

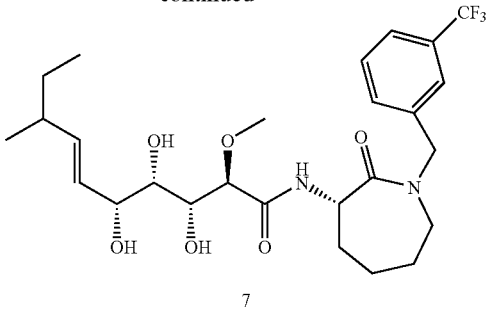

7

3.5 mL of methanol, 40 mg (61 μmol) of compound 6 and 26 mg (189 μmol, 3.1 eq.) of potassium carbonate are successively introduced into a 10 ml round-bottomed flask equipped with a magnetic stirrer. The reaction medium is stirred for 2 hours at room temperature and then taken up in 10 ml of ethyl acetate and 5 ml of saturated aqueous ammonium chloride solution. After separation of the phases by settling, the aqueous phase is re-extracted with ethyl acetate. The organic phases are combined and dried over sodium sulfate. After filtering and evaporating to dryness, 32 mg (99%) of the expected product 7 are obtained.

1H NMR spectrum (400 MHz)-δ in ppm-DMSO-d6, mixture of isomers (70%-30%): 0.81 (t, J=7.5 Hz, 2.1H); 0.82 (t, J=7.5 Hz, 0.9H); 0.92 (d, J=7.0 Hz, 0.9H); 0.93 (d, J=7.0 Hz, 2.1H); 1.10 (m, 1H); from 1.20 to 1.31 (m, 2H); 1.39 (m, 1H); 1.66 (m, 2H); 1.80 (m, 1H); 1.90 (m, 1H); 1.99 (m, 1H); from 3.21 to 3.38 (masked m, 2H); 3.27 (s, 3H); from 3.55 to 3.68 (m, 2H); 3.72 (d, J=7.5 Hz, 1H); 3.98 (m, 1H); 4.36 (d, J=5.5 Hz, 1H); 4.42 (d, J=7.0 Hz, 0.7H); 4.44 (d, J=7.0 Hz, 0.3H); 4.55 (d, J=4.5 Hz, 1H); 4.58 (d, J=15.0 Hz, 1H); 4.66 (dd, J=6.5 and 11.0 Hz, 1H); 4.70 (d, J=15.0 Hz, 1H); 5.37 (m, 1H); 5.48 (dd, J=7.5 and 15.5 Hz, 1H); from 7.54 to 7.66 (m, 4H); 7.93 (d, J=6.5 Hz, 1H).

ES: 531 (+)=(M+H)(+)

EXAMPLE 8

N-[(S)-2-oxo-1-(4-trifluoromethoxybenzyl)perhydroazepin-3-yl]-(E)-(2R,3R,4S,5R)-3,4,5-triacetoxy-2-methoxy-8-methyldec-6-enamide

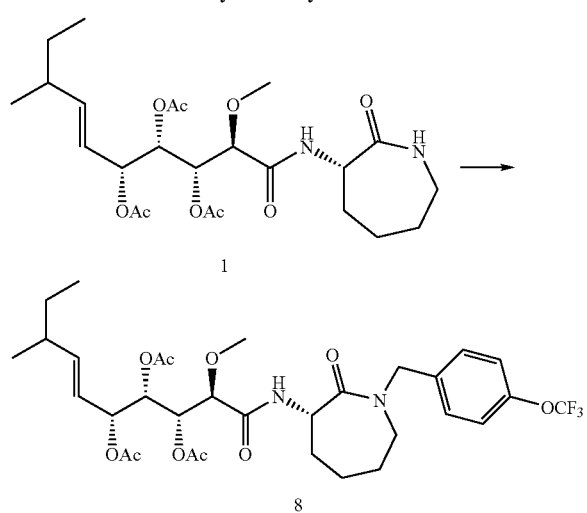

1 mL of 4-methyl-2-pentanone and 50 mg (100 μmol) of compound 1, 128 mg (500 μmol) of 4-trifluoromethoxybenzyl bromide and 163 mg (500 μmol) of anhydrous cesium carbonate are successively introduced into a 5 ml round-bottomed flask equipped with a magnetic stirrer, and under an argon atmosphere. The reaction medium is heated for 48 hours at 50° C. It is allowed to cool to room temperature and is then poured into a suspension of 10 ml of ethyl acetate and 5 ml of saturated aqueous ammonium chloride solution. After separation of the phases by settling, the aqueous phase is re-extracted with twice 10 ml of ethyl acetate. The organic phases are combined and dried over sodium sulfate. After filtering and evaporating to dryness, 180 mg of crude product are obtained, which product is purified by preparative chromatography (SiO2 60, 8 g 40-60 μm Biotage cartridge, eluent: EtOAc/heptane (50/50). 25 mg (37%) of the expected product 8 are obtained.

EXAMPLE 9

N-[(S)-2-oxo-1-(4-trifluoromethoxybenzyl)perhydroazepin-3-yl]-(E)-(2R,3R,4S,5R)-3,4,5-trihydroxy-2-methoxy-8-methyldec-6-enamide

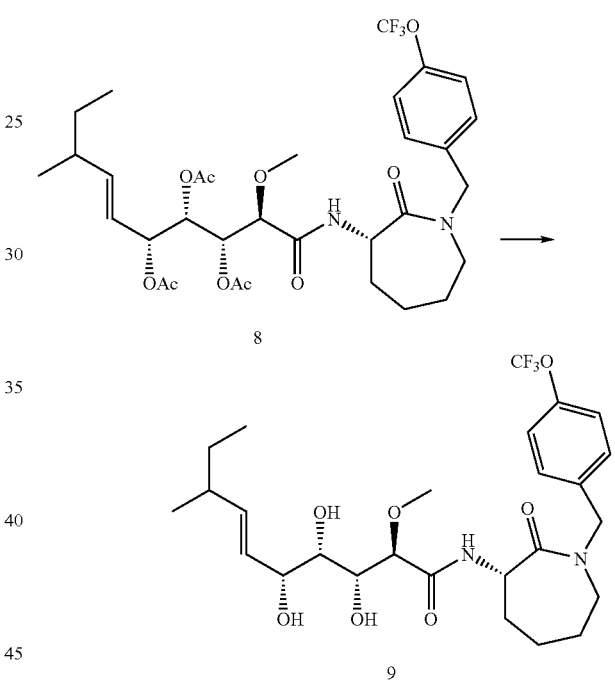

3 ml of methanol, 25 mg (37 μmol) of compound 8 and 16 mg (116 μmol, 3.1 eq.) of potassium carbonate are successively introduced into a 10 ml round-bottomed flask equipped with a magnetic stirrer. The reaction medium is stirred for 3 hours at room temperature and then taken up in ethyl acetate and saturated aqueous ammonium chloride solution. After separation of the phases by settling, the organic phase is dried over sodium sulfate. After filtering and evaporating to dryness, 19 mg (94%) of the expected product 9 are obtained.

1H NMR spectrum (400 MHz)-δ in ppm-DMSO-d6, mixture of isomers (70%-30%): 0.81 (t, J=7.5 Hz, 2.1H); 0.82 (t, J=7.5 Hz, 0.9H); 0.92 (d, J=7.0 Hz, 0.9H); 0.93 (d, J=7.0 Hz, 2.1H); from 1.04 to 1.51 (m, 4H); from 1.56 to 2.05 (m, 5H); from 3.21 to 3.39 (partially masked m, 2H); 3.28 (s, 3H); from 3.53 to 3.66 (m, 2H); 3.72 (d, J=7.0 Hz, 1H); 3.98 (m, 1H); 4.35 (d, J=5.5 Hz, 1H); from 4.40 to 4.70 (m, 5H); from 5.30 to 5.56 (m, 2H); 7.32 (broad d, J=8.5 Hz, 2H); 7.40 (broad d, J=8.5 Hz, 2H); 7.91 (d, J=6.5 Hz, 1H).

ES: 547(+)=(M+H)(+)

EXAMPLE 10

N-[(S)-1-(4-fluoro-3-trifluoromethylbenzyl)-2-oxoperhydroazepin-3-yl]-(E)-(2R,3R,4S,5R)-3,4,5-triacetoxy-2-methoxy-8-methyldec-6-enamide

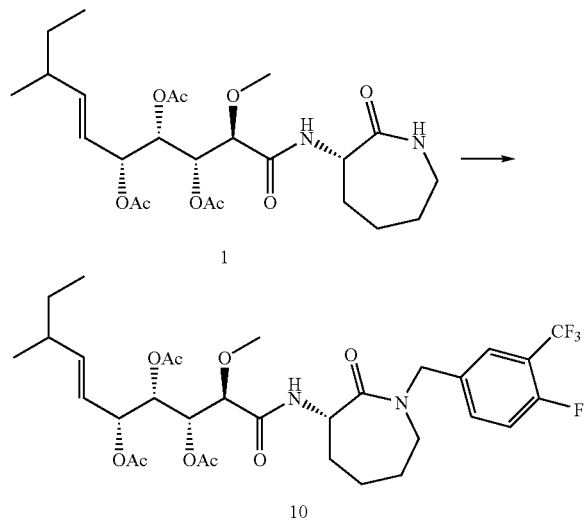

2.5 ml of 4-methyl-2-pentanone and 50 mg (100 μmol) of compound 1, 129 mg (500 μmol) of 4-fluoro-3-trifluoromethylbenzyl bromide and 163 mg (500 μmol) of anhydrous cesium carbonate are successively introduced into a 10 ml round-bottomed flask equipped with a magnetic stirrer, and under an argon atmosphere. The reaction medium is heated for 24 hours at 50° C. It is allowed to cool to room temperature and is then poured into a suspension of 10 ml of ethyl acetate and 5 ml of saturated aqueous ammonium chloride solution. After separation of the phases by settling, the aqueous phase is re-extracted with ethyl acetate. The organic phases are combined and dried over sodium sulfate. After filtering and evaporating to dryness, 140 mg of crude product are obtained, which product is purified by preparative chromatography (SiO₂ 60, 8 g 40-60 μm Biotage cartridge, eluent: EtOAc/heptane (50/50). 29 mg (43%) of the expected product 10 are obtained (Rf: 0.20).

EXAMPLE 11

N-[(S)-1-(4-fluoro-3-trifluoromethylbenzyl)-2-oxoperhydroazepin-3-yl]-(E)-(2R,3R,4S,5R)-3,4,5-trihydroxy-2-methoxy-8-methyldec-6-enamide

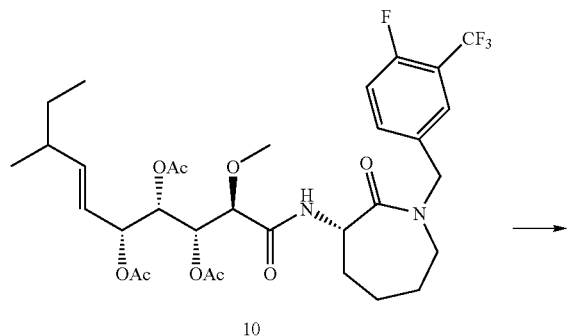

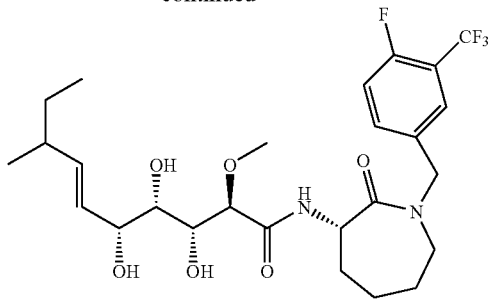

3.0 ml of methanol, 28 mg (42 μmol) of compound 10 and 18 mg (129 μmol, 3.1 eq.) of potassium carbonate are successively introduced into a 10 ml round-bottomed flask equipped with a magnetic stirrer. The reaction medium is stirred for 2 hours at room temperature and then taken up in 10 ml of ethyl acetate and 5 ml of saturated aqueous ammonium chloride solution. After separation of the phases by settling, the aqueous phase is re-extracted with ethyl acetate. The organic phases are combined and dried over sodium sulfate. After filtering and evaporating to dryness, 30 mg of product are obtained in the form of a yellow lacquer, which product is purified by preparative chromatography (Chromabond RS6 SiOH cartridge, eluent: 95/5 CH₂Cl₂/MeOH). 17 mg (75%) of product 11 are obtained (Rf 0.2).

1H NMR spectrum (400 MHz)-δ in ppm-DMSO-d6, mixture of isomers (70%-30%): 0.80 (t, J=7.5 Hz, 2.1H); 0.82 (t, J=7.5 Hz, 0.9H); 0.92 (d, J=7.0 Hz, 0.9H); 0.93 (d, J=7.0 Hz, 2.1H); 1.10 (m, 1H); from 1.20 to 1.31 (m, 2H); 1.38 (m, 1H); from 1.59 to 1.72 (m, 2H); 1.81 (m, 1H); 1.89 (m, 1H); 1.99 (m, 1H); 3.25 to 3.38 (partially masked m, 2H); 3.28 (s, 3H); from 3.56 to 3.65 (m, 2H); 3.72 (d, J=7.5 Hz, 1H); 3.98 (m, 1H); 4.37 (d, J=6.0 Hz, 1H); 4.42 (d, J=7.0 Hz, 0.7H); 4.44 (d, J=7.0 Hz, 0.3H); from 4.51 to 4.57 (m, 2H); 4.64 (m, 1H); 4.68 (d, J=15.0 Hz, 1H); 5.37 (m, 1H); 5.48 (dd, J=7.5 and 15.5 Hz, 1H); 7.48 (dd, J=8.5 and 11.0 Hz, 1H); from 7.62 to 7.71 (m, 2H); 7.93 (d, J=6.5 Hz, 1H).

ES: 549(+)=(M+H)(+)

EXAMPLE 12

N-[(S)-1-(4-fluorobenzyl)-2-oxoperhydroazepin-3-yl]-(E)-(2R,3R,4S,5R)-3,4,5-triacetoxy-2-methoxy-8-methyldec-6-enamide

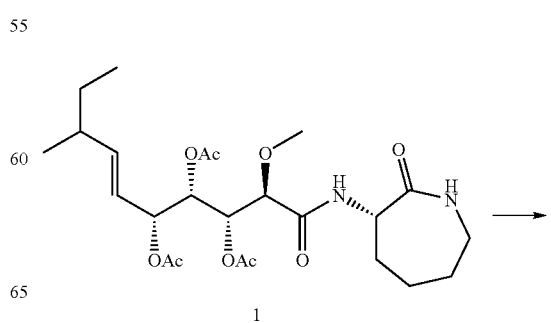

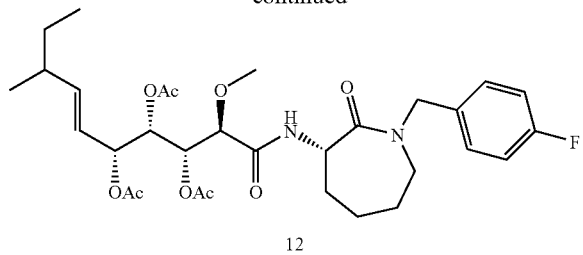

12

1 mL of 4-methyl-2-pentanone and 50 mg (100 μmol) of compound 1, 95 mg (500 μmol) of 4-fluorobenzyl bromide and 163 mg (500 μmol) of anhydrous cesium carbonate are successively introduced into a 10 ml round-bottomed flask equipped with a magnetic stirrer, and under an argon atmosphere. The reaction medium is heated for 24 hours at 50° C. It is allowed to cool to room temperature and is then poured into a suspension of 10 ml of ethyl acetate and 5 ml of saturated aqueous ammonium chloride solution. After separation of the phases by settling, the aqueous phase is re-extracted twice with 10 ml of ethyl acetate. The organic phases are combined and dried over sodium sulfate. After filtering and evaporating to dryness, 300 mg of crude product are obtained, which product is purified by preparative chromatography ($SiO_2$ 60, 20 g 40-60 μm Biotage cartridge, eluent: EtOAc/heptane (55/45). 45 mg (74%) of the expected product 12 are obtained (Rf: 0.30).

1H NMR spectrum (400 MHz)-δ in ppm-DMSO-d6, mixture of isomers (70%-30%): 0.76 (t, J=7.5 Hz, 0.9H); 0.79 (t, J=7.5 Hz, 2.1H); 0.88 (d, J=7.0 Hz, 3H); 1.08 (m, 1H); from 1.17 to 1.30 (m, 2H); 1.37 (m, 1H); 1.65 (m, 2H); 1.81 (m, 2H); from 1.94 to 2.00 (masked m, 1H); 1.97 (s, 3H); from 2.01 to 2.04 (m, 6H); from 3.21 to 3.30 (partially masked m, 1H); 3.33 (s, 3H); 3.57 (dd, J=10.5 and 15.0 Hz, 1H); 3.83 (d, J=4.5 Hz, 0.3H); 3.84 (d, J=4.5 Hz, 0.7H); 4.50 (d, J=14.5 Hz, 1H); 4.55 (m, 1H); 4.60 (d, J=14.5 Hz, 1H); from 5.20 to 5.39 (m, 4H); 5.55 (m, 1H); 7.13 (broad t, J=9.0 Hz, 2H); 7.33 (broad dd, J=6.0 and 9.0 Hz, 1H); 7.99 (d, J=6.5 Hz, 1H).

ES: 607(+)=(M+H)(+); 547(+)=(M+H)(+)—$CH_3COOH$

EXAMPLE 13

N-[(S)-1-(4-fluorobenzyl)-2-oxoperhydroazepin-3-yl]-(E)-(2R,3R,4S,5R)-3,4,5-trihydroxy-2-methoxy-8-methyldec-6-enamide

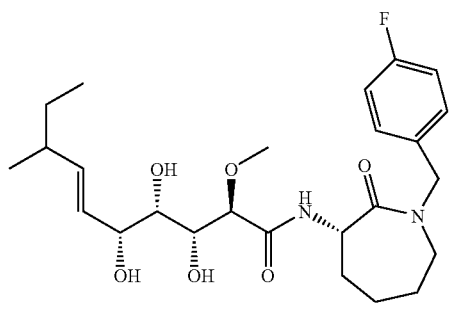

13

3.0 ml of methanol, 33 mg (54 μmol) of compound 12 and 24 mg (173 μmol, 3.2 eq.) of potassium carbonate are successively introduced into a 10 ml round-bottomed flask equipped with a magnetic stirrer. The reaction medium is stirred for 2 hours at room temperature and then concentrated, extracted with 3 times 5 ml of methylene chloride, and washed with 3 ml of water and then with saturated sodium chloride solution. The combined organic phases are dried over sodium sulfate, filtered and evaporated to dryness. 23 mg (89%) of product 13 are obtained.

1H NMR spectrum (400 MHz)-δ in ppm-DMSO-d6, mixture of isomers (70%-30%): 0.82 (t, J=7.5 Hz, 2.1H); 0.84 (t, J=7.5 Hz, 0.9H); 0.93 (d, J=7.0 Hz, 0.9H); 0.94 (d, J=7.0 Hz, 2.1H); 1.08 (m, 1H); from 1.20 to 1.31 (m, 2H); 1.38 (m, 1H); 1.65 (m, 2H); 1.79 (m, 1H); 1.88 (m, 1H); 1.99 (m, 1H); from 3.16 to 3.33 (masked m, 4H); 3.36 (broad d, J=7.0 Hz, 1H); 3.57 (dd, J=11.0 and 15.0 Hz, 1H); 3.61 (dd, J=2.5 and 7.5 Hz, 1H); 3.71 (d, J=7.0 Hz, 1H); 3.99 (t, J=7.0 Hz, 1H); from 4.08 to 4.77 (very broad m, 3H); 4.50 (d, J=14.5 Hz, 1H); 4.57 (d, J=14.5 Hz, 1H); 4.61 (m, 1H); 5.38 (m, 1H); 5.49 (dd, J=7.0 and 15.0 Hz, 1H); 7.15 (broad t, J=9.0 Hz, 2H); 7.32 (broad dd, J=5.5 and 9.0 Hz, 2H); 7.89 (d, J=6.5 Hz, 1H).

IC: 481(+)=(M+H)(+)

EXAMPLE 14

N-[(S)-1-(3,5-difluorobenzyl)-2-oxoperhydroazepin-3-yl]-(E)-(2R,3R,4S,5R)-3,4,5-triacetoxy-2-methoxy-8-methyldec-6-enamide

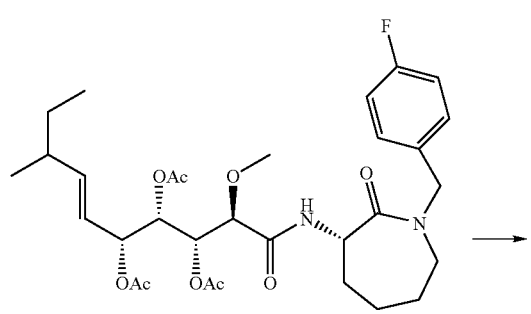

12

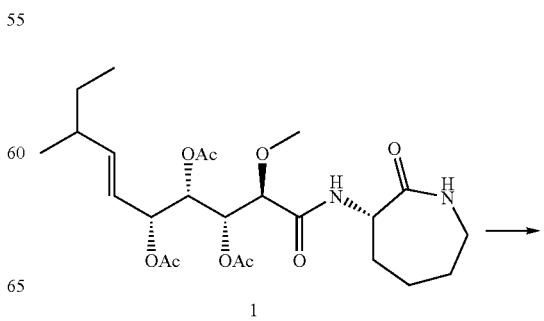

1

-continued

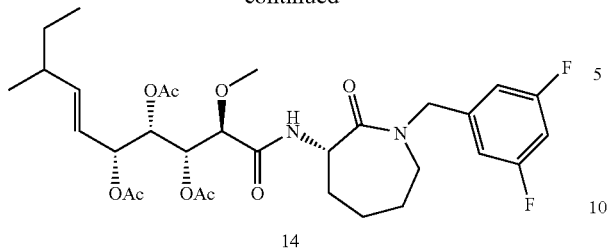

14

1 mL of 4-methyl-2-pentanone and 50 mg (100 μmol) of compound 1, 104 mg (502 μmol) of 3,5-difluorobenzyl bromide and 163 mg (502 μmol) of anhydrous cesium carbonate are successively introduced into a 10 ml round-bottomed flask equipped with a magnetic stirrer, and under an argon atmosphere. The reaction medium is heated for 24 hours at 50° C. It is allowed to cool to room temperature and is then poured into a suspension of 10 ml of ethyl acetate and 5 ml of saturated aqueous ammonium chloride solution. After separation of the phases by settling, the aqueous phase is re-extracted twice with 10 ml of ethyl acetate. The organic phases are combined and dried over magnesium sulfate. After filtering and evaporating to dryness, 290 mg of crude product are obtained, which product is purified by preparative chromatography ($SiO_2$ 60, 20 g 40-60 μm Biotage cartridge, eluent: EtOAc/heptane (55/45). 35 mg (56%) of the expected product 14 are obtained (Rf: 0.25).

1H NMR spectrum (400 MHz)-δ in ppm-DMSO-d6, mixture of isomers (70%-30%): 0.75 (t, J=7.5 Hz, 0.9H); 0.76 (t, J=7.5 Hz, 2.1H); 0.87 (d, J=7.0 Hz, 3H); from 1.11 to 1.30 (m, 3H); 1.39 (m, 1H); 1.69 (m, 2H); 1.84 (m, 2H); from 1.92 to 2.00 (masked m, 1H); 1.97 (s, 3H); from 2.00 to 2.04 (m, 6H); 3.25 (partially masked m, 1H); 3.33 (s, 3H); 3.63 (dd, J=11.5 and 15.5 Hz, 1H); 3.84 (d, J=4.5 Hz, 0.3H); 3.85 (d, J=4.5 Hz, 0.7H); 4.40 (d, J=15.5 Hz, 1H); 4.60 (m, 1H); 4.76 (d, J=15.5 Hz, 1H); from 5.21 to 5.39 (m, 4H); 5.54 (m, 1H); from 6.96 to 7.03 (m, 2H); 7.11 (tt, J=2.5 and 9.5 Hz, 1H); 7.98 (d, J=6.5 Hz, 1H).

ES: 625(+)=(M+H)(+); 565(+)=(M+H)(+)—$CH_3COOH$

EXAMPLE 15

N-[(S)-2-oxo-1-(3,5-difluorobenzyl)perhydroazepin-3-yl]-(E)-(2R,3R,4S,5R)-3,4,5-trihydroxy-2-methoxy-8-methyldec-6-enamide

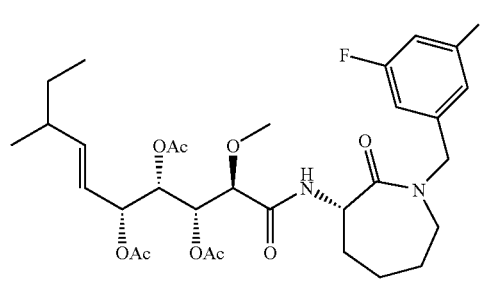

14

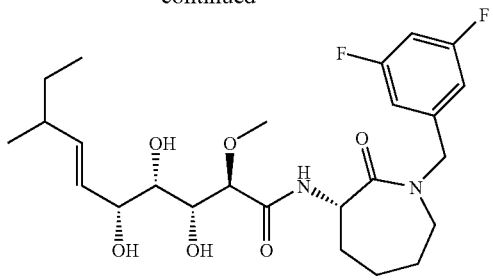

15

3 ml of methanol, 32 mg (51 μmol) of compound 14 and 22 mg (159 μmol, 3.1 eq.) of potassium carbonate are successively introduced into a 10 ml round-bottomed flask equipped with a magnetic stirrer. The reaction medium is stirred for 3 hours at room temperature and is then taken up in ethyl acetate and saturated aqueous ammonium chloride solution. After separation of the phases by settling, the organic phase is dried over sodium sulfate. After filtering and evaporating to dryness, 25 mg (98%) of the expected product 15 are obtained.

1H NMR spectrum (400 MHz)-δ in ppm-DMSO-d6, mixture of isomers (70%-30%): 0.81 (t, J=7.5 Hz, 2.1H); 0.82 (t, J=7.5 Hz, 0.9H); 0.92 (d, J=7.0 Hz, 0.9H); 0.93 (d, J=7.0 Hz, 2.1H); from 1.08 to 1.46 (m, 4H); 1.67 (m, 2H); from 1.77 to 1.92 (m, 2H); 1.99 (m, 1H); from 3.19 to 3.39 (masked m, 2H); 3.27 (s, 3H); 3.59 (dd, J=2.5 and 7.5 Hz, 1H); 3.64 (dd, J=11.0 and 15.0 Hz, 1H); 3.71 (d, J=7.5 Hz, 1H); 3.98 (t, J=7.0 Hz, 1H); from 4.13 to 4.73 (very broad m, 3H); 4.43 (d, J=15.5 Hz, 1H); 4.66 (m, 1H); 4.70 (d, J=15.5 Hz, 1H); 5.38 (m, 1H); 5.48 (dd, J=7.5 and 15.5 Hz, 1H); 6.99 (m, 2H); 7.13 (tt, J=2.5 and 9.5 Hz, 1H); 7.92 (d, J=6.5 Hz, 1H).

ES: 499(+)=(M+H)(+)

EXAMPLE 16

N-[(S)-1-(3,4-difluorobenzyl)-2-oxoperhydroazepin-3-yl]-(E)-(2R,3R,4S,5R)-3,4,5-triacetoxy-2-methoxy-8-methyldec-6-enamide

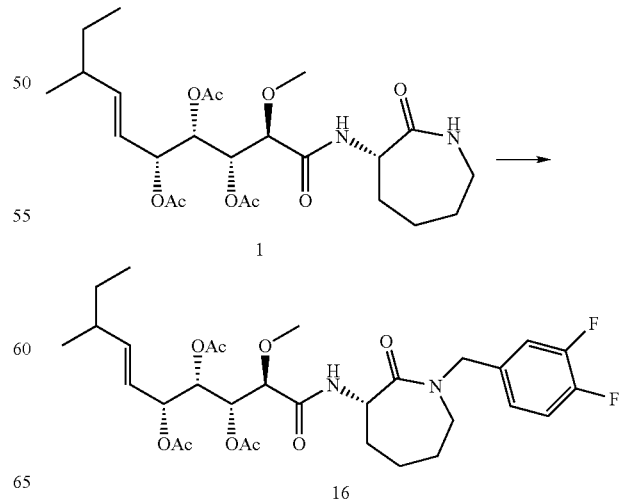

1.5 mL of 3-methyl-2-butanone and 70 mg (140 µmol) of compound 1, 146 mg (700 µmol) of 3,4-difluorobenzyl bromide and 230 mg (700 µmol) of anhydrous cesium carbonate are successively introduced into a 10 ml round-bottomed flask equipped with a magnetic stirrer, and under an argon atmosphere. The reaction medium is heated for 48 hours at 60° C. The reaction medium is allowed to cool to room temperature, and 10 ml of methylene chloride and 5 ml of water are poured into the suspension. After separation of the phases by settling, the organic phase is dried over sodium sulfate. After filtering and evaporating to dryness, 165 mg of crude product are obtained, which product is purified by preparative chromatography (SiO$_2$ 60, 8 g 40-60 µm Biotage cartridge, eluent: EtOAc/heptane (50/50). 25 mg (29%) of the expected product 16 are obtained (Rf: 0.15).

1H NMR spectrum (400 MHz)-δ in ppm-DMSO-d6, mixture of isomers (70%-30%) 0.75 (t, J=7.5 Hz, 0.9H); 0.76 (t, J=7.5 Hz, 2.1H); 0.87 (d, J=7.0 Hz, 3H); from 1.06 to 1.28 (m, 3H); 1.38 (m, 1H); 1.67 (m, 2H); 1.82 (m, 2H); from 1.93 to 2.00 (masked m, 1H); 1.97 (s, 3H); from 2.01 to 2.04 (m, 6H); from 3.21 to 3.48 (partially masked m, 1H); 3.32 (s, 3H); 3.58 (dd, J=11.5 and 15.0 Hz, 1H); 3.83 (d, J=4.5 Hz, 0.3H); 3.84 (d, J=4.5 Hz, 0.7H); 4.43 (d, J=15.0 Hz, 1H); 4.56 (m, 1H); 4.67 (d, J=15.0 Hz, 1H); from 5.20 to 5.38 (m, 4H); 5.53 (m, 1H); 7.13 (m, 1H); from 7.29 to 7.41 (m, 2H); 7.98 (d, J=6.5 Hz, 1H).

IC: 642(+)=(M+NH$_4$)(+); 565 (+)=(M+H)(+)—CH$_3$COOH

EXAMPLE 17

N-[(S)-1-(3,4-difluorobenzyl)-2-oxoperhydroazepin-3-yl]-(E)-(2R,3R,4S,5R)-3,4,5-trihydroxy-2-methoxy-8-methyldec-6-enamide

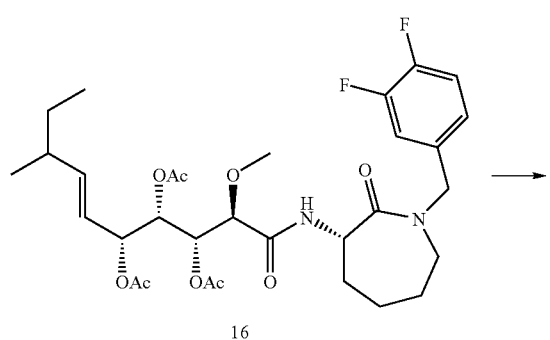

3.0 ml of methanol, 25 mg (40 µmol) of compound 16 and 18 mg (130 µmol, 3.3 eq.) of potassium carbonate are successively introduced into a 10 ml round-bottomed flask equipped with a magnetic stirrer. The reaction medium is stirred for 3 hours at room temperature and then extracted with methylene chloride and washed with water. After drying over sodium sulfate, filtering and evaporating to dryness, 17 mg (85%) of product 17 are obtained.

ES: 499(+)=(M+H)(+)

EXAMPLE 18

N-[(S)-2-oxo-1-(2,3,5,6-tetrafluorobenzyl)perhydroazepin-3-yl]-(E)-(2R,3R,4S,5R)-3,4,5-triacetoxy-2-methoxy-8-methyldec-6-enamide

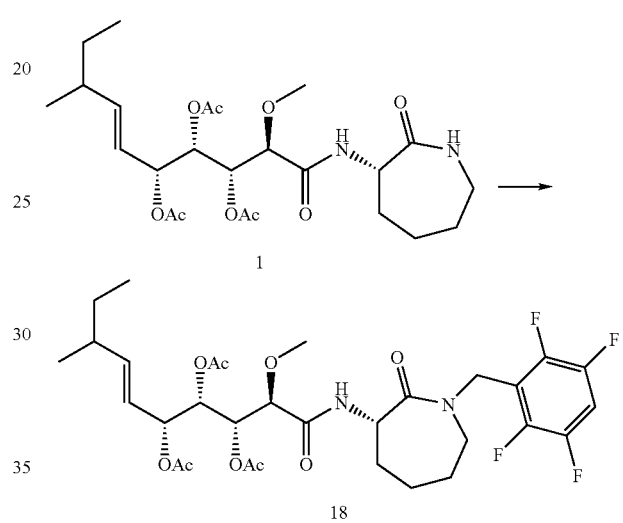

2 mL of 3-methyl-2-butanone and 100 mg (200 µmol) of compound 1, 199 mg (1.0 mmol) of 2,3,5,6-tetrafluorobenzyl bromide and 327 mg (1.0 mmol) of anhydrous cesium carbonate are successively introduced into a 10 ml round-bottomed flask equipped with a magnetic stirrer, and under an argon atmosphere. The reaction medium is heated for 24 hours at 80° C. The reaction medium is allowed to cool to room temperature, and 10 ml of methylene chloride and 5 ml of water are added to the suspension. After separation of the phases by settling, the organic phase is dried over sodium sulfate. After filtering and evaporating to dryness, 125 mg of crude product are obtained, which product is purified by preparative chromatography (SiO$_2$ 60, 8 g 40-60 µm Biotage cartridge, eluent: EtOAc/heptane (50/50). 15 mg (11%) of the expected product 18 are obtained (Rf: 0.20).

1H NMR spectrum (400 MHz)-δ in ppm-DMSO-d6, mixture of isomers (70%-30%): 0.76 (t, J=7.5 Hz, 3H); 0.87 (t, J=7.0 Hz, 0.9H); 0.88 (d, J=7.0 Hz, 2.1H); from 1.06 to 1.41 (m, 4H); from 1.51 to 1.87 (masked m, 4H); from 1.91 to 2.05 (m, 7H); 1.92 (s, 3H); from 3.15 to 3.55 (partially masked m, 1H); 3.29 (s, 3H); 3.64 (m, 1H); 3.81 (d, J=4.5 Hz, 1H); 4.52 (m, 1H); from 4.67 to 4.76 (m, 2H); from 5.19 to 5.37 (m, 4H); 5.51 (m, 1H); 7.84 (m, 1H); 7.94 (d, J=6.5 Hz, 1H).

ES: 661(+)=(M+H)(+); 601(+)=(M+H)(+)—CH$_3$COOH

EXAMPLE 19

N-[(S)-1-(2,3,5,6-tetrafluorobenzyl)-2-oxoperhydroazepin-3-yl]-(E)-(2R,3R,4S,5R)-3,4,5-trihydroxy-2-methoxy-8-methyldec-6-enamide

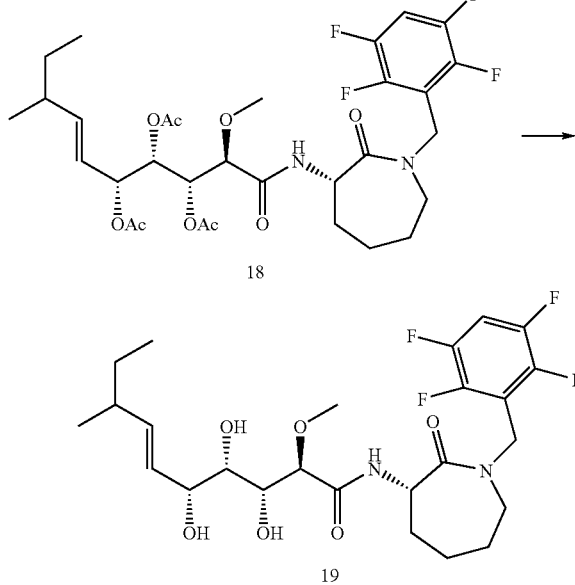

3.0 ml of methanol, 22 mg (33 μmol) of compound 18 and 14 mg (100 μmol, 3.0 eq.) of potassium carbonate are successively introduced into a 10 ml round-bottomed flask equipped with a magnetic stirrer. The reaction medium is stirred for 2 hours at room temperature and then extracted with methylene chloride and washed with water. After drying over sodium sulfate, filtering and evaporating to dryness, 15 mg (84%) of product 19 are obtained.

1H NMR spectrum (400 MHz)-δ in ppm-DMSO-d6, mixture of isomers (70%-30%): 0.79 (t, J=7.5 Hz, 2.1H); 0.81 (t, J=7.5 Hz, 0.9H); 0.91 (d, J=7.0 Hz, 0.9H); 0.93 (d, J=7.0 Hz, 2.1H); from 1.10 to 1.42 (m, 4H); from 1.57 to 1.81 (m, 4H); 1.98 (m, 1H); from 3.16 to 3.40 (partially masked m, 2H); 3.25 (s, 3H); from 3.53 to 3.72 (m, 3H); 3.96 (m, 1H); 4.36 (d, J=6.0 Hz, 1H); 4.42 (m, 1H); 4.56 (m, 2H); 4.66 (d, J=15.0 Hz, 1H); 4.74 (d, J=15.0 Hz, 1H); 5.35 (m, 1H); 5.47 (m, 1H); from 7.79 to 7.89 (m, 2H).

ES: 535(+)=(M+H)(+)

EXAMPLE 20

N-[(S)-2-oxo-1-(2,3,4,5,6-pentafluorobenzyl)perhydroazepin-3-yl]-(E)-(2R,3R,4S,5R)-3,4,5-triacetoxy-2-methoxy-8-methyldec-6-enamide

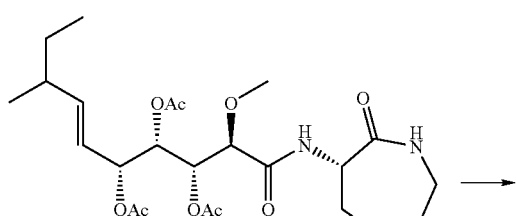

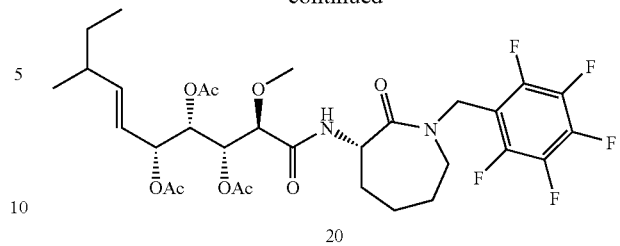

1.5 mL of 3-methyl-2-butanone and 60 mg (120 μmol) of compound 1, 172 mg (659 mmol) of 2,3,4,5,6-pentafluorobenzyl bromide and 196 mg (602 mmol) of anhydrous cesium carbonate are successively introduced into a 10 ml round-bottomed flask equipped with a magnetic stirrer, and under an argon atmosphere. The reaction medium is heated for 12 h at 50° C. Next, a further 172 mg (659 mmol) of 2,3,4,5,6-pentafluorobenzyl bromide and 196 mg (602 mmol) of anhydrous cesium carbonate are added to the medium, which is heated for 48 hours, and a further 172 mg (659 mmol) of 2,3,4,5,6-pentafluorobenzyl bromide and 196 mg (602 mmol) of anhydrous cesium carbonate are added to the medium, which is heated for 12 hours at 50° C. Ethyl acetate and water are poured into the suspension. After separation of the phases by settling, the organic phase is dried over magnesium sulfate. After filtering and evaporating to dryness, the crude product is purified by preparative chromatography (SiO₂ 60, 4 g 40-60 μm RS cartridge, eluent: EtOAc/heptane (55/45). 29 mg (35%) of the expected product 20 are obtained (Rf: 0.26).

1H NMR spectrum (400 MHz)-δ in ppm-DMSO-d6, mixture of isomers (70%-30%): 0.81 (t, J=7.5 Hz, 0.9H); 0.82 (t, J=7.5 Hz, 2.1H); 0.92 (d, J=7.0 Hz, 0.9H); 0.94 (d, J=7.0 Hz, 2.1H); from 1.12 to 1.64 (partially masked m, 4H); from 1.75 to 1.95 (m, 3H); 2.01 (partially masked m, 1H); 2.03 (s, 3H); 2.05 (s, 3H); 2.09 (s, 0.9H); 2.10 (s, 2.1H); 3.31 (m, 1H); 3.40 (s, 3H); 3.59 (m, 1H); 3.78 (d, J=4.5 Hz, 0.3H); 3.80 (d, J=4.5 Hz, 0.7H); 4.57 (m, 1H); 4.71 (d, J=15.5 Hz, 1H); 4.78 (d, J=15.5 Hz, 1H); from 5.23 to 5.43 (m, 3H); 5.53 (m, 2H); 5.62 (dd, J=7.5 and 15.5 Hz, 1H); 7.91 (d, J=6.5 Hz, 1H).

ES: 679(+)=(M+H)(+); 619(+)=(M+H)(+)—CH₃COOH

EXAMPLE 21

N-[(S)-1-(2,3,4,5,6-pentafluorobenzyl)-2-oxoperhydroazepin-3-yl]-(E)-(2R,3R,4S,5R)-3,4,5-trihydroxy-2-methoxy-8-methyldec-6-enamide

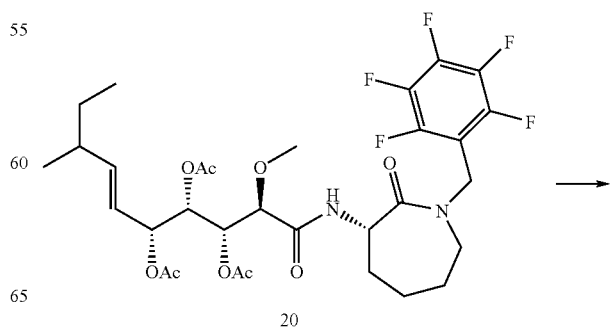

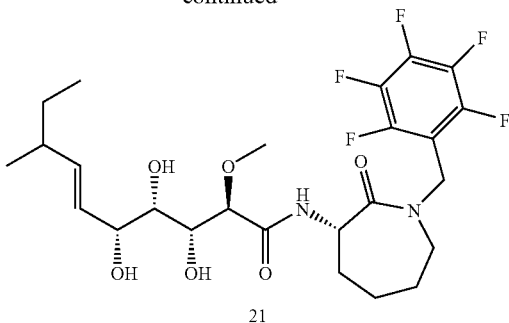

21

2.50 ml of methanol, 28.5 mg (42 µmol) of compound 20 and 18 mg (130 µmol, 3.1 eq.) of potassium carbonate are successively introduced into a 10 ml round-bottomed flask equipped with a magnetic stirrer. The reaction medium is stirred for 2 hours at room temperature and then extracted with ethyl acetate and washed with water. After drying over magnesium sulfate, filtering and evaporating to dryness, 13 mg (57%) of product 21 are obtained.

1H NMR spectrum (400 MHz)-δ in ppm-DMSO-d6, mixture of isomers (70%-30%): 0.79 (t, J=7.5 Hz, 2.1H); 0.81 (t, J=7.5 Hz, 0.9H); 0.91 (d, J=7.0 Hz, 0.9H); 0.93 (d, J=7.0 Hz, 2.1H); from 1.11 to 1.40 (m, 4H); from 1.57 to 1.90 (m, 4H); 1.98 (m, 1H); from 3.23 to 3.36 (partially masked m, 2H); 3.25 (s, 3H); from 3.52 to 3.68 (m, 2H); 3.70 (d, J=7.5 Hz, 1H); 3.96 (m, 1H); 4.35 (d, J=5.5 Hz, 1H); 4.40 (m, 1H); from 4.52 to 4.59 (m, 2H); from 4.64 to 4.72 (m, 2H); 5.36 (m, 1H); 5.46 (dd, J=7.5 and 15.5 Hz, 1H); 7.84 (d, J=6.5 Hz, 1H).

ES: 553(+)=(M+H)(+)

EXAMPLE 22

N-[(S)-2-oxo-1-(4-cyano-3-fluorobenzyl)perhydroazepin-3-yl]-(E)-(2R,3R,4S,5R)-3,4,5-triacetoxy-2-methoxy-8-methyldec-6-enamide

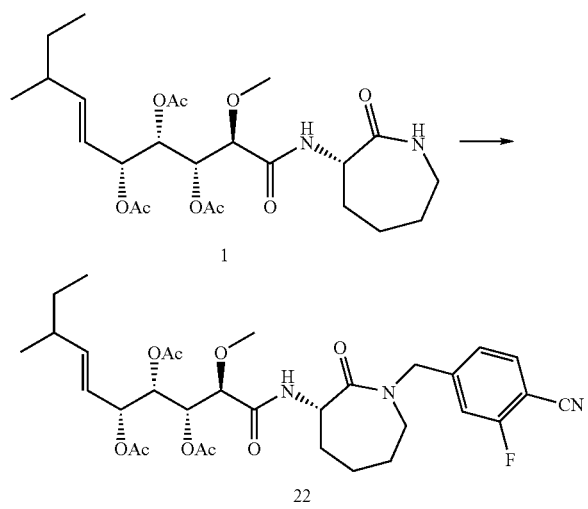

15 mL of 3-methyl-2-butanone and 800 mg (1.6 mmol) of compound 1, 1.72 g (8.0 mmol) of 4-cyano-3-fluorobenzyl and 2.61 g (8.0 mmol) of anhydrous cesium carbonate are successively introduced into a 50 ml round-bottomed flask equipped with a magnetic stirrer, and under an argon atmosphere. The reaction medium is heated for 24 hours at 50° C. Ethyl acetate (100 ml) and water (70 ml) are poured into the suspension. After separation of the phases by settling, the organic phase is washed with 70 ml of water and dried over magnesium sulfate. After filtering and evaporating to dryness, the crude product (2.4 g) is purified by preparative chromatography (SiO$_2$ 60, 20 g 40-60 µm RS cartridge, eluent: EtOAc/heptane gradient. 227 mg (22%) of the expected product 22 are obtained.

ES: 654(+)=(M+Na)(+)

1H NMR spectrum (400 MHz)-δ in ppm-DMSO-d6, mixture of isomers (80%-20%): 0.74 (t, J=7.5 Hz, 0.6H); 0.75 (t, J=7.5 Hz, 2.4H); 0.86 (d, J=7.0 Hz, 2.4H); 0.87 (d, J=7.0 Hz, 0.6H); from 1.12 to 1.29 (m, 3H); 1.42 (m, 1H); from 1.57 to 1.76 (m, 2H); from 1.79 to 1.88 (m, 2H); from 1.90 to 2.00 (m, 1H); 1.96 (s, 2.4H); 1.97 (s, 0.6H); 2.01 (s, 2.4H); 2.02 (s, 0.6H); 2.03 (s, 0.6H); 2.04 (s, 2.4H); from 3.22 to 3.35 (partially masked m, 1H); 3.31 (s, 0.6H); 3.32 (s, 2.4H); 3.66 (m, 1H); 3.84 (d, J=4.5 Hz, 0.2H); 3.85 (d, J=4.5 Hz, 0.8H); 4.49 (d, J=16.0 Hz, 1H); 4.61 (m, 1H); 4.85 (d, J=16.0 Hz, 1H); from 5.20 to 5.38 (m, 4H); 5.52 (dd, J=8.0 and 15.5 Hz, 0.8H); 5.54 (dd, J=8.0 and 15.0 Hz, 0.2H); 7.32 (dd, J=1.5 and 8.0 Hz, 1H); 7.41 (dd, J=1.5 and 10.5 Hz, 1H); 7.88 (dd, J=7.0 and 8.0 Hz, 1H); 7.97 (d, J=6.5 Hz, 1H).

EXAMPLE 23

N-[(S)-1-(4-cyano-3-fluorobenzyl)-2-oxoperhydroazepin-3-yl]-(E)-(2R,3R,4S,5R)-3,4,5-trihydroxy-2-methoxy-8-methyldec-6-enamide

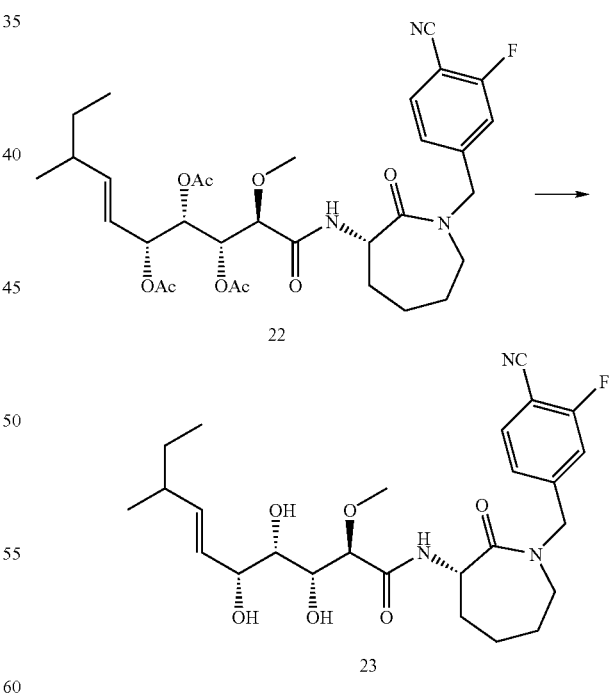

8.0 ml of methanol, 128 mg (203 µmol) of compound 22 and 90 mg (648 µmol, 3.1 eq.) of potassium carbonate are successively introduced into a 50 ml round-bottomed flask equipped with a magnetic stirrer. The reaction medium is stirred for 10 minutes at room temperature, poured into 20 ml of saturated NH$_4$Cl solution and then extracted with ethyl acetate (twice 25 ml). The aqueous phase is saturated with NaCl and extracted with 20 ml of CH₂Cl₂. The organic phases are combined and evaporated to dryness. 164 mg of crude product are obtained, which product is chromatographed on a silica cartridge (9 g, eluent: CH₂Cl₂/isopropanol gradient: isopropanol 0 to 10%) to give 77 mg (75%) of product 23.

ES: 506(+)=(M+H)(+)

1H NMR spectrum (400 MHz)-δ in ppm-DMSO-d6, mixture of isomers (80%-20%): 0.80 (t, J=7.5 Hz, 2.4H); 0.82 (t, J=7.5 Hz, 0.6H); 0.92 (d, J=7.0 Hz, 0.6H); 0.93 (d, J=7.0 Hz, 2.4H); from 1.11 to 1.32 (m, 3H); 1.42 (m, 1H); from 1.60 to 1.74 (m, 2H); from 1.77 to 1.92 (m, 2H); 1.98 (m, 1H); from 3.21 to 3.38 (partially masked m, 2H); 3.21 (s, 3H); from 3.55 to 3.74 (m, 2H); 3.71 (d, J=7.5 Hz, 1H); 3.97 (m, 1H); 4.37 (d, J=6.0 Hz, 1H); 4.42 (m, 1H); 4.50 (d, J=16.0 Hz, 1H); 4.55 (d, J=4.5 Hz, 1H); 4.68 (m, 1H); 4.79 (d, J=16.0 Hz, 1H); 5.37 (m, 1H); 5.48 (dd, J=7.5 and 15.5 Hz, 1H); 7.30 (dd, J=1.5 and 8.0 Hz, 1H); 7.70 (dd, J=1.5 and 10.5 Hz, 1H); from 7.87 to 7.93 (m, 2H).

EXAMPLE 24

N-[(S)-2-oxo-1-(3-cyano-4-fluorobenzyl)perhydroazepin-3-yl-(E)-(2R,3R,4S,5R)-3,4,5-triacetoxy-2-methoxy-8-methyldec-6-enamide

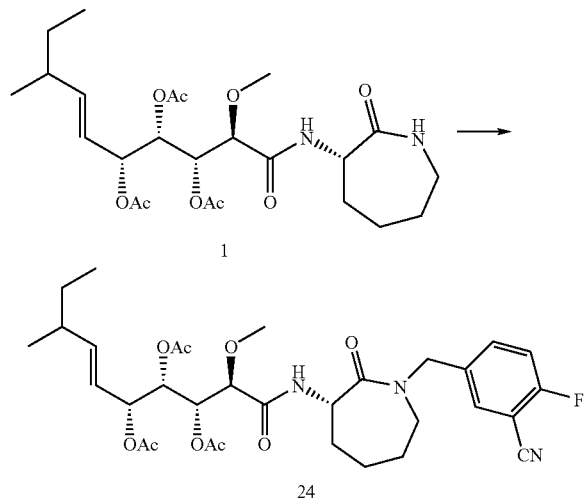

10 mL of 3-methyl-2-butanone and 630 mg (1.26 mmol) of compound 1, 1.35 g (6.3 mmol) of 3-cyano-4-fluorobenzyl bromide and 2.05 g (6.3 mmol) of anhydrous cesium carbonate are successively introduced into a 50 ml round-bottomed flask equipped with a magnetic stirrer, and under an argon atmosphere. The reaction medium is heated for 24 hours at 50° C. The reaction medium is allowed to cool to room temperature, filtered through a sinter funnel and evaporated to dryness. The crude product (1.83 g) is purified by preparative chromatography (SiO₂ 60, 20 g 40-60 μm RS cartridge, eluent: EtOAc/heptane gradient). 298 mg (47%) of the expected product 24 are obtained.

ES: 654(+)=(M+Na)(+)

1H NMR spectrum (400 MHz)-δ in ppm-DMSO-d6, mixture of isomers (80%-20%): 0.74 (t, J=7.5 Hz, 0.6H); 0.75 (t, J=7.5 Hz, 2.4H); 0.86 (d, J=7.0 Hz, 2.4H); 0.87 (d, J=7.0 Hz, 0.6H); from 1.10 to 1.26 (m, 3H); 1.41 (m, 1H); from 1.58 to 1.74 (m, 2H); from 1.78 to 1.88 (m, 2H); from 1.90 to 2.00 (partially masked m, 1H); 1.97 (s, 2.4H); 1.98 (s, 0.6H); 2.01 (s, 2.4H); 2.02 (s, 0.6H); 2.03 (s, 0.6H); 2.04 (s, 2.4H); from 3.23 to 3.36 (partially masked m, 1H); 3.32 (s, 0.6H); 3.33 (s, 2.4H); 3.62 (m, 1H); 3.85 (d, J=4.5 Hz, 0.2H); 3.86 (d, J=4.5 Hz, 0.8H); 4.42 (d, J=15.0 Hz, 1H); 4.59 (m, 1H); 4.77 (d, J=16.0 Hz, 1H); from 5.21 to 5.38 (m, 4H); 5.53 (dd, J=8.0 and 15.5 Hz, 1H); 7.48 (t, J=9.0 Hz, 1H); 7.69 (ddd, J=2.5-5.5 and 9.0 Hz, 1H); 7.81 (dd, J=2.5 and 6.5 Hz, 1H); 7.91 (d, J=6.5 Hz, 1H).

EXAMPLE 25

N-[(S)-1-(3-cyano-4-fluorobenzyl)-2-oxoperhydroazepin-3-yl]-(E)-(2R,3R,4S,5R)-3,4,5-trihydroxy-2-methoxy-8-methyldec-6-enamide

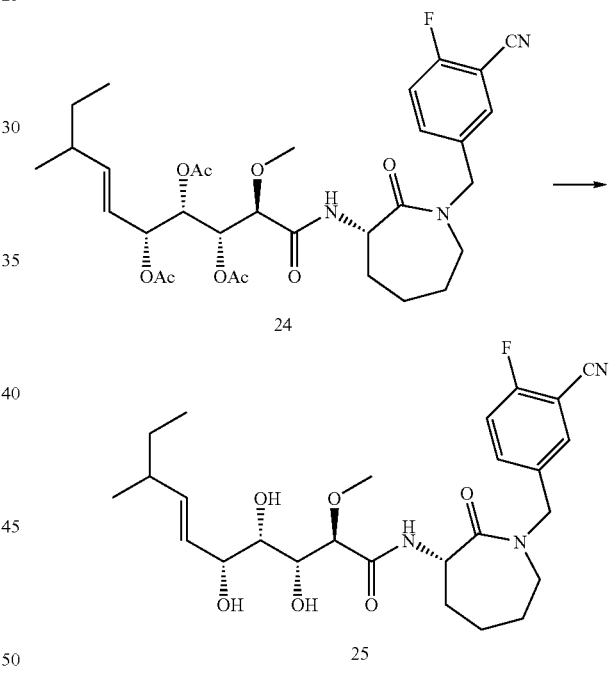

10.0 ml of methanol, 267 mg (423 μmol) of compound 24 and 187 mg (1.35 mmol, 3.2 eq.) of potassium carbonate are successively introduced into a 50 ml round-bottomed flask equipped with a magnetic stirrer. The reaction medium is stirred for 10 minutes at room temperature, poured into 100 ml of saturated NH₄Cl solution and then extracted with ethyl acetate (twice 100 ml). The aqueous phase is saturated with NaCl and extracted with 100 ml of EtOAc. The organic phases are combined and evaporated to dryness. 226 mg of crude product are obtained, which product is chromatographed on a silica cartridge (9 g, eluent: CH₂Cl₂/isopropanol gradient: isopropanol 0 to 10%) to give 121 mg (57%) of expected product 25.

ES: 506(+)=(M+H)(+)

1H NMR spectrum (400 MHz)-δ in ppm-DMSO-d6, mixture of isomers (80%-20%): 0.80 (t, J=7.5 Hz, 2.4H); 0.82 (t, J=7.5 Hz, 0.6H); 0.92 (d, J=7.0 Hz, 0.6H); 0.93 (d, J=7.0 Hz, 2.4H); 1.14 (m, 1H); from 1.20 to 1.30 (m, 2H); 1.40 (m, 1H); from 1.60 to 1.71 (m, 2H); from 1.76 to 1.94 (m, 2H); 1.98 (m, 1H); from 3.24 to 3.37 (partially masked m, 2H); 3.27 (s, 3H); from 3.55 to 3.67 (m, 2H); 3.71 (d, J=7.5 Hz, 1H); 3.98 (m, 1H); 4.32 (d, J=4.0 Hz, 0.2H); 4.39 (broad m, 1H); 4.45 (partially masked m, 1H); 4.46 (d, J=15.0 Hz, 1H); 4.57 (broad m, 0.8H); 4.65 (m, 1H); 4.69 (d, J=15.0 Hz, 1H); 5.37 (m, 1H); 5.49 (dd, J=7.5 and 15.5 Hz, 1H); 7.50 (t, J=9.0 Hz, 1H); 7.68 (ddd, J=2.5-5.5 and 9.0 Hz, 1H); 7.81 (dd, J=2.5 and 6.5 Hz, 1H); 7.90 (d, J=6.5 Hz, 1H).

EXAMPLE 26

N-[(S)-1-(3-amino-1H-indazol-6-ylmethyl)-2-oxoperhydroazepin-3-yl]-(E)-(2R,3R,4S,5R)-3,4,5-trihydroxy-2-methoxy-8-methyldec-6-enamide

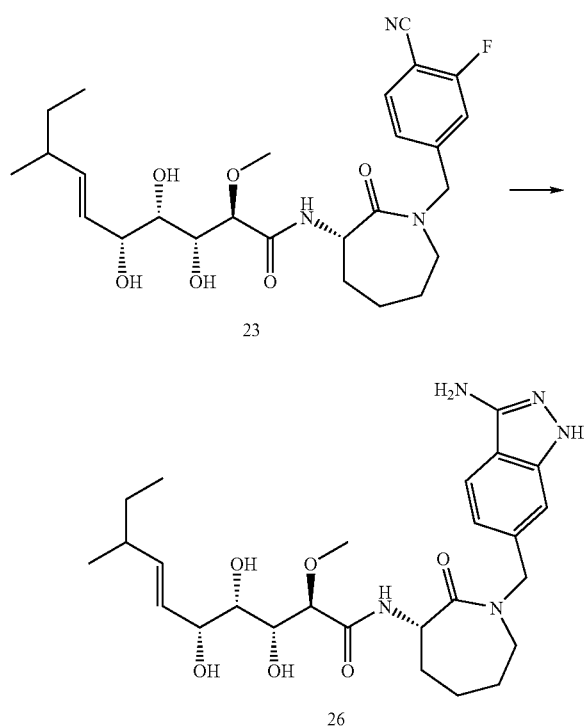

1.0 ml of butanol, 30 mg (59 µmol) of compound 23 and 5.9 mg (119 µmol) of hydrazine hydrate are successively introduced into a 2 ml microwave tube equipped with a magnetic stirrer. The reaction medium is stirred for 30 minutes at 180° C. The reaction medium is poured into isopropyl ether (10 ml) and precipitates are formed, and are filtered off. After drying under vacuum, 3.45 mg (11%) of expected product 26 are obtained (white solid).

TLC: 90/10 CH$_2$Cl$_2$/i-Propanol; Rf: 0.15

ES: 517(+)=(M+H)(+)

EXAMPLE 27

N-[(S)-1-(3-amino-1H-indazol-5-ylmethyl)-2-oxoperhydroazepin-3-yl]-(E)-(2R,3R,4S,5R)-3,4,5-trihydroxy-2-methoxy-8-methyldec-6-enamide

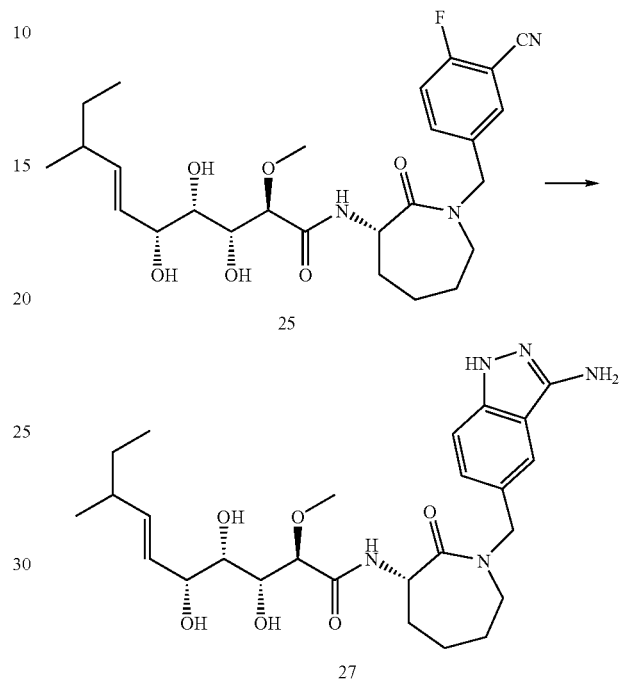

0.73 ml of butanol, 22 mg (44 µmol) of compound 23 and 4.3 mg (87 µmol) of hydrazine hydrate are successively introduced into a 2 ml microwave tube equipped with a magnetic stirrer. The reaction medium is stirred for 30 minutes at 180° C. The reaction medium is poured into isopropyl ether (10 ml) and precipitates are formed, and are filtered off. After drying under vacuum, 2.2 mg (9.7%) of expected product 27 are obtained (white solid).

TLC: 90/10 CH$_2$Cl$_2$/MeOH; Rf: 0.20

ES: 517(+)=(M+H)(+)

Antiproliferative Activity of the Products Prepared

The antiproliferative activity of product 3 was determined by measuring the inhibition of cell proliferation of Hep-G2 cells. The cells are subcultured in a cell culture medium at a concentration of 1000 cells per well, and incubated for 4 hours at 37° C. and 5% CO$_2$.

Medium used for the Hep-G2 cell culture: Dubelcco's modified Eagle's medium/Ham mixture F12 (Gibco); NEAA (10%; nonessential amino acids, Gibco); sodium pyruvate (1%, Gibco); L-glutamine (1%, Gibco); fetal calf serum (5%; PAA).

After 4 hours, the test products dissolved in a DMSO/cell culture medium mixture are added at various concentrations and the resulting mixtures are incubated for 72 hours at 37° C. and 5% CO$_2$. The intracellular ATP content was measured using the CellTiterGlo test reagent (Promega).

The results of the cell proliferation tests are given in table 1 below:

TABLE 1

| Example | Structure | IC 50 (μM)/HEP G2 |
|---|---|---|
| Bengamide E | (structure) | 7.0 |
| 3 | (structure) | 0.02 |

The antiproliferative activity of the products of the examples of table 2 was determined by measuring the inhibition of the cellular proliferation of HCT116 cells. The cells are seeded in a cell culture medium at a concentration of 10 000 cells per well, in 0.17 mL of medium, and 20 μL of test product, at various concentrations, and 10 μL of Thymidine [methyl-14C] (100 μCi/ml-specific activity 47.90 mCi/mmol; NEN Technologies reference NEC568 batch 3550-001) are added, and the cells are then incubated at 37° C. and 5% $CO_2$.

Medium used for culturing the HCT116 cells: DMEM medium, 2 mM L-glutamine, 200 IU/ml penicillin, 200 pg/ml streptomycin and 10% (V/V) fetal calf serum (Life Technologies).

After 48 hours, the incorporation of $^{14}C$-thymidine is counted in a 1450 Microbeta Wallac Trilux liquid scintillation counter. The results R are expressed in cpm (counts per minute) and converted to a percentage of growth inhibition GI % by first subtracting the mean of the number of cpm of the wells without B cells and by then dividing the number of cpm of the wells of the untreated cells C comprising 20 μL of product dilution medium containing 1% ethanol. (GI %=(R−B)×100/C %).

The IC50 values are calculated using equation 205 of XLFit software (IDBS Company, UK) by nonlinear regression analysis using Marquardt algorithm (Donald W. Marquardt, J. Soc. Industry Appl., vol. 11, No. 2, June, 1963).

The products of table 2 have an IC50 on the HCT116 cells of generally less than 30 μM and preferably less than 100 nM.

TABLE 2

| Example | Structure |
|---|---|
| 5 | (structure) |
| 7 | (structure) |

TABLE 2-continued
| Example | Structure |
|---|---|
| 9 | 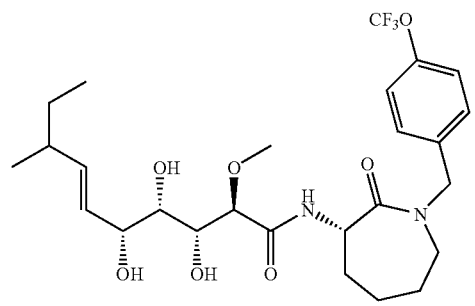 |
| 11 | 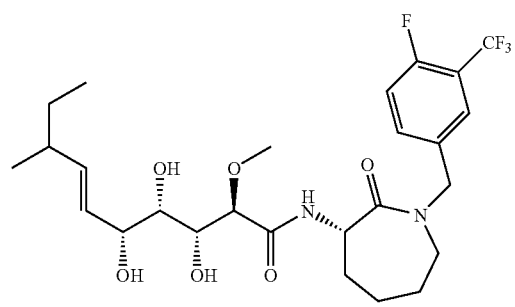 |
| 13 | 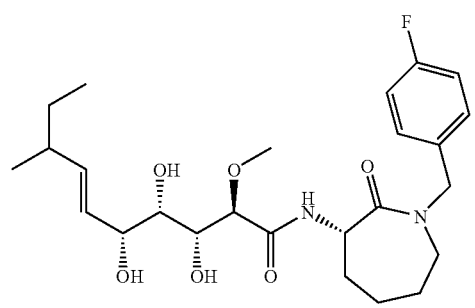 |
| 15 | 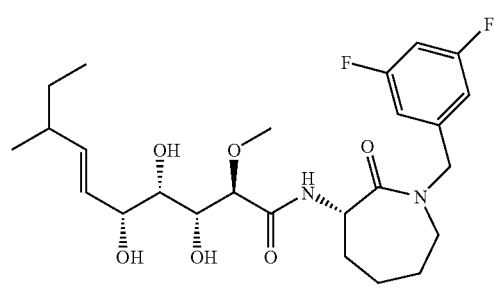 |
| 17 | 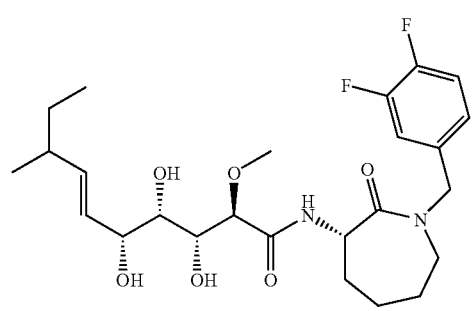 |

TABLE 2-continued
| Example | Structure |
|---|---|
| 19 | 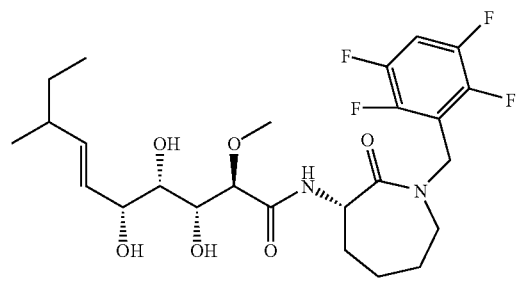 |
| 21 | 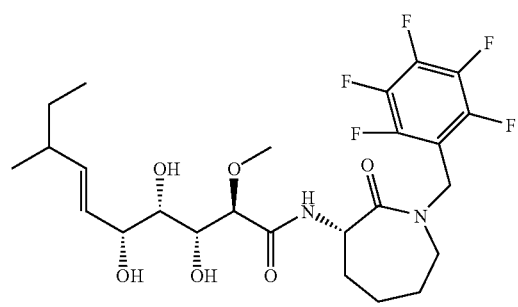 |
| 23 | 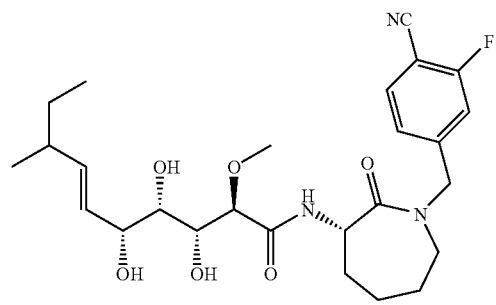 |
| 25 | 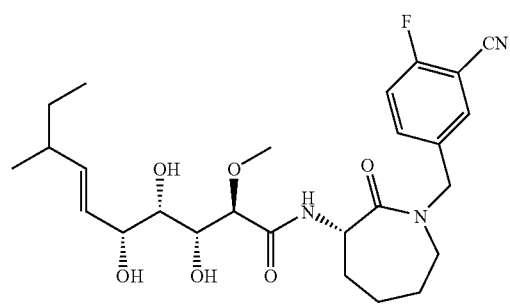 |
| 26 | 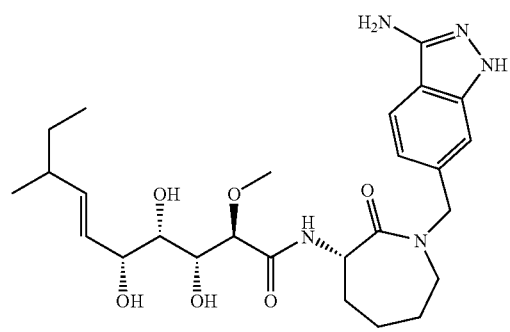 |

TABLE 2-continued

| Example | Structure |
|---|---|
| 27 | 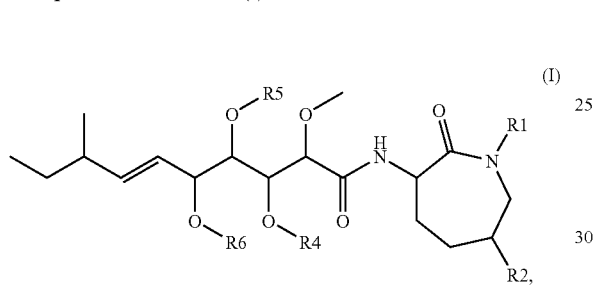 |

The invention claimed is:

1. A product of formula (I):

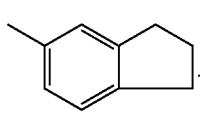
(I)

wherein

R1 is —(C1-C8)alkylaryl, or —(C1-C8)alkylheteroaryl, the aryl or heteroaryl portion of which is substituted with 0 to 5 substituents R8, which may be identical or different, chosen from H, halogen, alkyl, haloalkyl, O-haloalkyl, $NH_2$, aryl and heteroaryl, where aryl of aryl and alkylaryl are, independently, monocyclic or polycyclic aromatic substituents containing from 6 to 14 carbon atoms, and where heteroaryl of heteroaryl and alkylheteroaryl are, independently, monocylic or polycyclic heteroaromatic substituents containing from 1 to 13 carbon atoms and from 1 to 4 heteroatoms selected from sulfur, oxygen, nitrogen and selenium;

R2 is independently selected from the group consisting of H and OH; and

R4, R5 and R6 are each independently selected from the group consisting of H and —(C1-C6)acyl.

2. A product according to claim 1, wherein R1 is a —(C1-C8)alkylaryl group in which aryl is

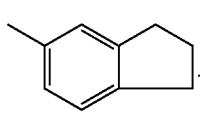

3. A product according to claim 1, wherein R1 is a —(C1-C8)alkylheteroaryl group in which heteroaryl is selected from the group consisting of:

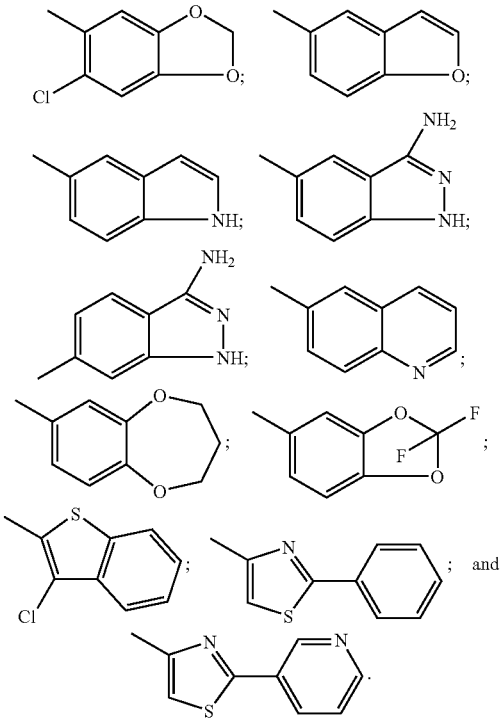

4. A product according to claim 1, wherein each of R4, R5 and R6 is H.

5. A product according to claim 1, wherein R2 is H.

6. A product of formula (II):

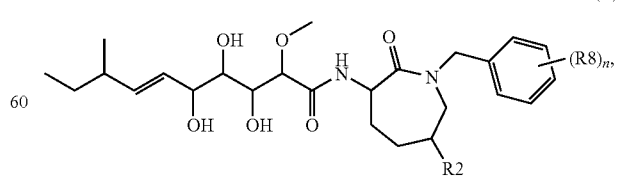
(II)

wherein:

R8 is independently selected from the group consisting of H, halogen, OH, CN, alkyl, haloalkyl, $NH_2$, aryl, heteroaryl, O(C1-C24)alkyl, O-haloalkyl, OCO(C1-C24)alkyl, —(C1-C4)alkylaryl, and —(C1-C4)alkylheteroaryl, where aryl of aryl and alkylaryl are, independently, monocyclic or polycyclic aromatic substituents containing from 6 to 14 carbon atoms, and where heteroaryl of heteroaryl and alkylheteroaryl are, independently, monocylic or polycyclic heteroaromatic substituents containing from 1 to 13 carbon atoms and from 1 to 4 heteroatoms selected from sulfur, oxygen, nitrogen and selenium;

n=0, 1, 2, 3, 4 or 5; and

R2 is selected from the group consisting of H and OH.

7. A product according to claim 6, wherein R8 is independently selected from the group consisting of H, —C(CH$_3$)$_3$, F, CF$_3$ and OCF$_3$.

8. A product according to claim 6 wherein n=4 or 5.

9. A product according to claim 7 wherein n=4 or 5.

10. A product according to claim 1, wherein the absolute conformation of the carbons bearing the substituents OCH$_3$, OR4, OR5 and OR6 is as shown in formula (III):

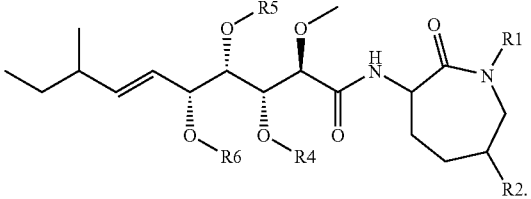

(III)

11. A product according to claim 6, which is

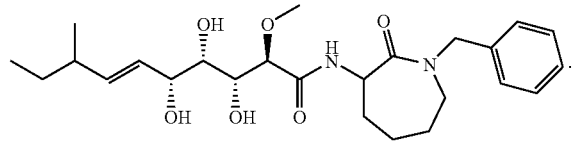

12. A product which is

N-[(S)-1-(4-benzyl)-2-oxoperhydroazepin-3-yl]-(E)-(2R,3R,4S,5R)-3,4,5-trihydroxy-2-methoxy-8-methyldec-6-enamide, N-[(S)-1-(4-tert-butylbenzyl)-2-oxoperhydroazepin-3-yl]-(E)-(2R,3R,4S,5R)-3,4,5-trihydroxy-2-methoxy-8-methyldec-6-enamide, N-[(S)-2-oxo-1-(3-trifluoromethylbenzyl)perhydroazepin-3-yl]-(E)-(2R,3R,4S,5R)-3,4,5-trihydroxy-2-methoxy-8-methyldec-6-enamide, N-[(S)-2-oxo-1-(4-trifluoromethoxybenzyl)perhydroazepin-3-yl]-(E)-(2R,3R,4S,5R)-3,4,5-trihydroxy-2-methoxy-8-methyldec-6-enamide, N-[(S)-1-(4-fluoro-3-trifluoromethyl benzyl)-2-oxoperhydroazepin-3-yl]-(E)-(2R,3R,4S,5R)-3,4,5-trihydroxy-2-methoxy-8-methyldec-6-enamide, N-[(S)-1-(4-fluorobenzyl)-2-oxoperhydroazepin-3-yl]-(E)-(2R,3R,4S,5R)-3,4,5-trihydroxy-2-methoxy-8-methyldec-6-enamide, N-[(S)-2-oxo-1-(3,5-difluorobenzyl)perhydroazepin-3-yl]-(E)-(2R,3R,4S,5R)-3,4,5-trihydroxy-2-methoxy-8-methyldec-6-enamide, N-[(S)-1-(3,4-difluorobenzyl)-2-oxoperhydroazepin-3-yl]-(E)-(2R,3R,4S,5R)-3,4,5-trihydroxy-2-methoxy-8-methyldec-6-enamide, N-[(S)-1-(2,3,5,6-tetrafluorobenzyl)-2-oxoperhydroazepin-3-yl]-(E)-(2R,3R,4S,5R)-3,4,5-trihydroxy-2-methoxy-8-methyldec-6-enamide, N-[(S)-1-(2,3,4,5,6-pentafluorobenzyl)-2-oxoperhydroazepin-3-yl]-(E)-(2R,3R,4S,5R)-3,4,5-trihydroxy-2-methoxy-8-methyldec-6-enamide, N-[(S)-1-(4-cyano-3-fluorobenzyl)-2-oxoperhydroazepin-3-yl]-(E)-(2R,3R,4S,5R)-3,4,5-trihydroxy-2-methoxy-8-methyldec-6-enamide, N-[(S)-1-(3-cyano-4-fluorobenzyl)-2-oxoperhydroazepin-3-yl]-(E)-(2R,3R,4S,5R)-3,4,5-trihydroxy-2-methoxy-8-methyldec-6-enamide, N-[(S)-1-(3-amino-1H-indazol-6-ylmethyl)-2-oxoperhydroazepin-3-yl]-(E)-(2R,3R,4S,5R)-3,4,5-trihydroxy-2-methoxy-8-methyldec-6-enamide, or N-[(S)-1-(3-amino-1H-indazol-5-ylmethyl)-2-oxoperhydroazepin-3-yl]-(E)-(2R,3R,4S,5R)-3,4,5-trihydroxy-2-methoxy-8-methyldec-6-enamide.

13. A product according to claim 1 which is in
racemic form;
a form enriched in one stereoisomer; or
a form enriched in one enantiomer; and which is optionally salified.

14. A process for preparing a product of formula (I)

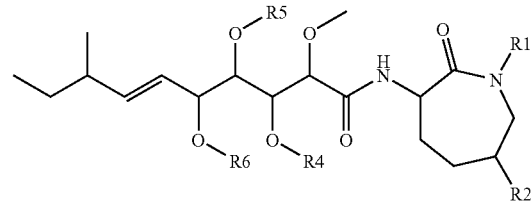

(I)

wherein:

(i) R1 is independently selected from the group consisting of H, —(C1-C24)alkyl, —(C3-C9)cycloalkyl, heterocycloalkyl, —(C3-C24)alkylene, heterocycloalkylene, aryl, heteroaryl, arylalkyl, heteroarylalkyl, arylalkylene, heteroarylalkylene, —(C1-C8)alkylaryl-(C1-C24)alkyl, —(C1-C8)alkylaryl-O—(C1-C24)alkyl, (ii) R2 is independently selected from the group consisting of H, OR7, OCO(R7), in which R7 is selected from the group consisting of —(C1-C24)alkyl, (C3-C9)cycloalkyl, heterocycloalkyl, —(C3-C24)alkylene, heterocycloalkylene, aryl, heteroaryl, arylalkyl, heteroarylalkyl, arylalkylene, heteroarylalkylene, —(C1-C8)alkylaryl-(C1-C24)alkyl, —(C1-C8)alkylaryl-O—(C1-C24)alkyl, (iii) R4, R5 and R6 are each independently selected from the group consisting of H, —(C1-C6)acyl, —(C1-C6)alkyl, —(C1-C6)alkylaryl, —(C1-C6)alkyl-heteroaryl, -aryl, -heteroaryl, -arylalkylene, -heteroarylalkylene, where heterocyclo of heterocycloalkyl and heterocycloalkylene are, independently, saturated or partially unsaturated cyclic hydrocarbon-based substituents containing 1 to 13 carbon atoms and from 1 to 3 hetero atoms, selected from N, O, S and Se, and where aryl of aryl, arylalkyl, arylalkylene and alkylaryl are, independently, monocyclic or polycyclic aromatic substituents containing from 6 to 14 carbon atoms, and where heteroaryl of heteroaryl, heteroarylalkyl and heteroarylalkylene are, independently, monocylic or polycyclic heteroaromatic substituents containing from 1 to 13 carbon atoms and from 1 to 4 heteroatoms selected from sulfur, oxygen, nitrogen and selenium;

comprising the steps of
1) culturing and growing of *Myxococcus virescens*,
2) extracting a bengamide-rich fraction of said culture,
3) introducing the substituents R1, R2, R4, R5 and R6 onto a product derived from the bengamide-rich fraction, to obtain a product of formula (I).

15. A process according to claim 14, further comprising a step of purifying the bengamide-rich fraction prior to step 3.

16. A process according to claim 14, wherein the bengamide-rich fraction comprises a product of formula (IV)

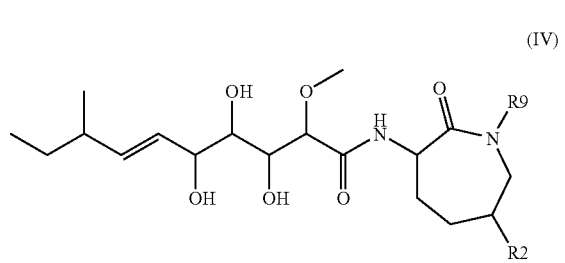

(IV)

wherein R9 is H or methyl, and R2 is H or OH.

17. A process according to claim 15, wherein the bengamide-rich fraction comprises a product of formula (IV)

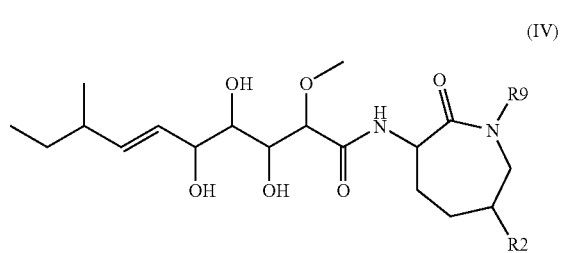

(IV)

wherein R9 is H or methyl, and R2 is H or OH.

18. A process according to claim 16 wherein step 3 of introducing the substituents R1, R2, R4, R5 and R6 comprises a step in which the substituent R1 is introduced onto the product of formula (IV) after protection of its free alcohol functions.

19. A process according to claim 17 wherein step 3 of introducing the substituents R1, R2, R4, R5 and R6 comprises a step in which the substituent R1 is introduced onto the product of formula (IV) after protection of its free alcohol functions.

20. A process for preparing a product of formula (II)

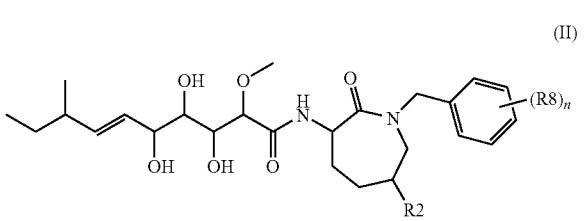

(II)

wherein R2 is H or OH, and R8 is selected from the group consisting of H, halogen, OH, CN, O(C1-C24)alkyl, OCO(C1-C24)alkyl, —(C1-C4)alkylaryl, and —(C1-C4)alkylheteroaryl, where aryl of alkylaryl is a monocyclic or polycyclic aromatic substituent containing from 6 to 14 carbon atoms, and where heteroaryl of alkylheteroaryl is a monocylic or polycyclic heteroaromatic substituents containing from 1 to 13 carbon atoms and from 1 to 4 heteroatoms selected from sulfur, oxygen, nitrogen and selenium; and n=0, 1, 2, 3,4 or 5;

comprising a step in which a product of formula (VI)

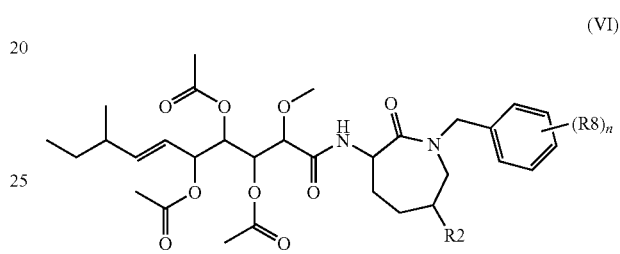

(VI)

wherein R2 is H or $OCOCH_3$, and R8 and n are as defined above, is saponified to obtain a product of general formula (II).

21. A process according to claim 20, wherein the product of formula (VI) is obtained by reaction between a product of formula (V)

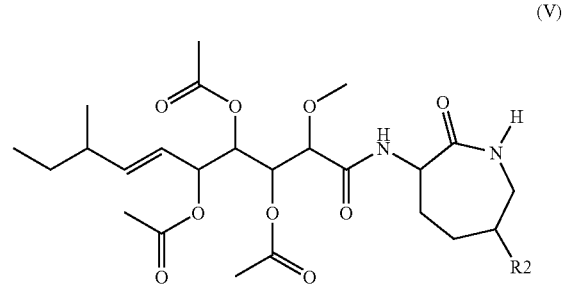

(V)

and a benzyl halide

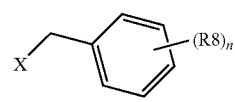

wherein X is a halogen and R8 and n are as defined above, in the presence of a base.

22. A process according to claim 21, wherein the product of formula (V) is obtained by acetylation of a product of formula (IV)

(IV)

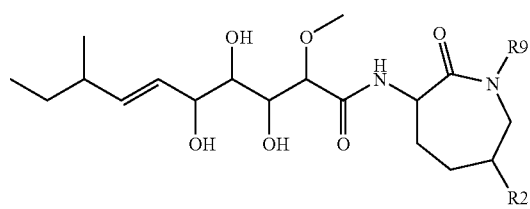

in which R9 is H and R2 is H or OH.

23. A process for preparing a product of the formula

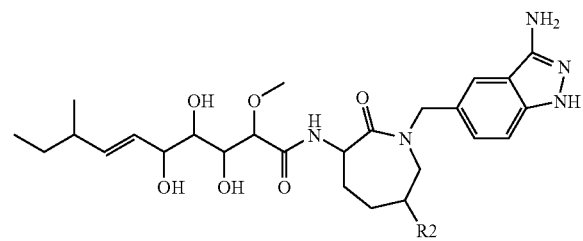

comprising a step in which a product of formula

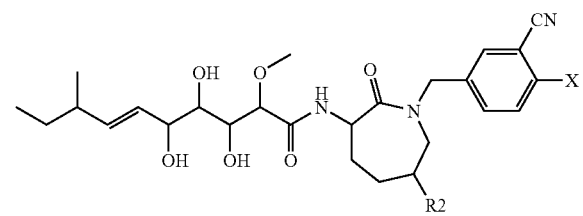

is placed in contact with NH$_2$—NH$_2$ in a solvent, and then heated.

24. A process for preparing a product of the formula

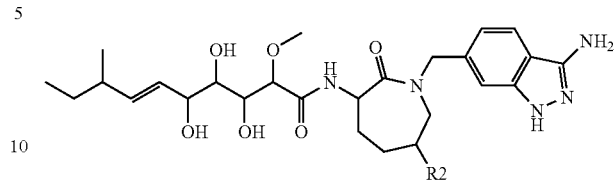

comprising a step in which a product of formula

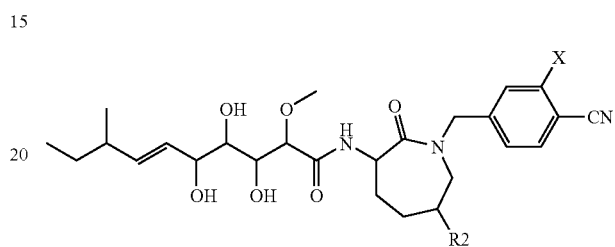

is placed in contact with NH$_2$—NH$_2$ in a solvent, and then heated.

25. A process according to claim 23 wherein the solvent is ethanol or butanol.

26. A process according to claim 24 wherein the solvent is ethanol or butanol.

27. A pharmaceutical composition comprising a product according to claim 1, in combination with a pharmaceutically acceptable excipient.

28. A pharmaceutical composition comprising a product according to claim 12, in combination with a pharmaceutically acceptable excipient.

* * * * *